US011883448B2

(12) United States Patent
Uchida et al.

(10) Patent No.: US 11,883,448 B2
(45) Date of Patent: Jan. 30, 2024

(54) ONCOLYTIC HSV VECTOR

(71) Applicant: University of Pittsburgh—Of the Commonwealth System of Higher Education, Pittsburgh, PA (US)

(72) Inventors: Hiroaki Uchida, Tokyo (JP); Justus B. Cohen, Allison Park, PA (US); Joseph C. Glorioso, III, Pittsburgh, PA (US); Paola Grandi, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 486 days.

(21) Appl. No.: 16/985,459

(22) Filed: Aug. 5, 2020

(65) Prior Publication Data

US 2021/0138007 A1   May 13, 2021

Related U.S. Application Data

(63) Continuation of application No. 16/746,145, filed on Jan. 17, 2020, now abandoned, which is a continuation of application No. 16/191,141, filed on Nov. 14, 2018, now Pat. No. 10,576,115, which is a continuation of application No. 15/616,585, filed on Jun. 7, 2017, now Pat. No. 10,172,893, which is a continuation of application No. 15/032,958, filed as application No. PCT/US2014/062676 on Oct. 28, 2014, now Pat. No. 10,201,575.

(60) Provisional application No. 61/896,497, filed on Oct. 28, 2013.

(51) Int. Cl.
*C12N 15/00* (2006.01)
*A61K 35/763* (2015.01)
*C12N 7/00* (2006.01)
*C07K 14/005* (2006.01)

(52) U.S. Cl.
CPC .......... *A61K 35/763* (2013.01); *C07K 14/005* (2013.01); *C12N 7/00* (2013.01); *C07K 2319/33* (2013.01); *C12N 2710/16621* (2013.01); *C12N 2710/16622* (2013.01); *C12N 2710/16632* (2013.01); *C12N 2710/16641* (2013.01); *C12N 2710/16643* (2013.01); *C12N 2710/16645* (2013.01); *C12N 2710/16662* (2013.01); *C12N 2710/16671* (2013.01)

(58) Field of Classification Search
None
See application file for complete search history.

(56) References Cited

U.S. PATENT DOCUMENTS

| | | |
|---|---|---|
| 5,059,538 A | 10/1991 | Nozaki et al. |
| 5,759,814 A | 6/1998 | Burke et al. |
| 5,804,413 A | 9/1998 | DeLuca |
| 5,849,572 A | 12/1998 | Glorioso et al. |
| 5,879,934 A | 3/1999 | DeLuca |
| 6,261,552 B1 | 7/2001 | DeLuca |
| 6,469,155 B1 | 10/2002 | Fiume et al. |
| 6,653,447 B1 | 11/2003 | Cosman et al. |
| 7,473,418 B2 | 1/2009 | Yu et al. |
| 7,514,252 B2 | 4/2009 | Chiocca et al. |
| 7,531,167 B2 | 5/2009 | Glorioso et al. |
| 8,129,167 B2 | 3/2012 | Cosman |
| 8,957,036 B2 | 2/2015 | Cascio et al. |
| 9,157,071 B2 | 10/2015 | Campadelli et al. |
| 9,593,347 B2 | 3/2017 | Glorioso, III et al. |
| 2002/0037575 A1 | 3/2002 | Speck |
| 2008/0008686 A1 | 1/2008 | Yao |
| 2008/0289058 A1 | 11/2008 | Cascio et al. |
| 2009/0136452 A1 | 5/2009 | Zhou et al. |
| 2010/0041737 A1 | 2/2010 | Naldini et al. |
| 2010/0233141 A1 | 9/2010 | Polach et al. |
| 2011/0213017 A1 | 9/2011 | Cascio et al. |
| 2013/0071430 A1 | 3/2013 | Nakamura et al. |
| 2013/0096186 A1 | 4/2013 | Glorioso, III et al. |
| 2013/0156808 A1 | 6/2013 | Jonjic |
| 2016/0153000 A1 | 6/2016 | Glorioso et al. |
| 2016/0250267 A1 | 9/2016 | Uchida et al. |
| 2017/0035819 A1 | 2/2017 | Uchida et al. |
| 2017/0274025 A1 | 3/2017 | Cascio et al. |
| 2017/0081384 A1 | 4/2017 | Glorioso, III et al. |
| 2017/0107537 A1 | 7/2017 | Glorioso, III et al. |
| 2017/0189514 A1 | 9/2017 | Uchida et al. |
| 2017/0274057 A1 | 9/2017 | Jonjic |

FOREIGN PATENT DOCUMENTS

| | | |
|---|---|---|
| CA | 2 476 724 A1 | 8/2004 |
| JP | 2001-508294 A | 6/2001 |
| JP | 2003-518080 A | 6/2003 |
| JP | 2009060907 A | 3/2009 |
| KR | 2003-0047667 A | 6/2003 |
| WO | WO 99/06583 A1 | 2/1999 |

(Continued)

OTHER PUBLICATIONS

Cheng, J. et al., Virology J., 2020, vol. 17, 11 pages.*

(Continued)

*Primary Examiner* — Michael D Burkhart
(74) *Attorney, Agent, or Firm* — Leydig, Voit & Mayer, Ltd.

(57) ABSTRACT

The present invention provides a recombinant oncolytic Herpes Simplex Virus (oHSV) comprising a non-HSV ligand specific for a molecule (protein, lipid, or carbohydrate determinant) present on the surface of a cell (such as a cancer cell) and one or more copies of one or more microRNA target sequences inserted into one or more HSV gene loci, preferably one or more HSV gene(s) required for replication of HSV in normal (i.e., non-cancerous) cells. The invention further provides stocks and pharmaceutical compositions comprising the inventive oHSV and methods for killing tumor cells employing the inventive oHSV.

49 Claims, 11 Drawing Sheets

Figure 1:
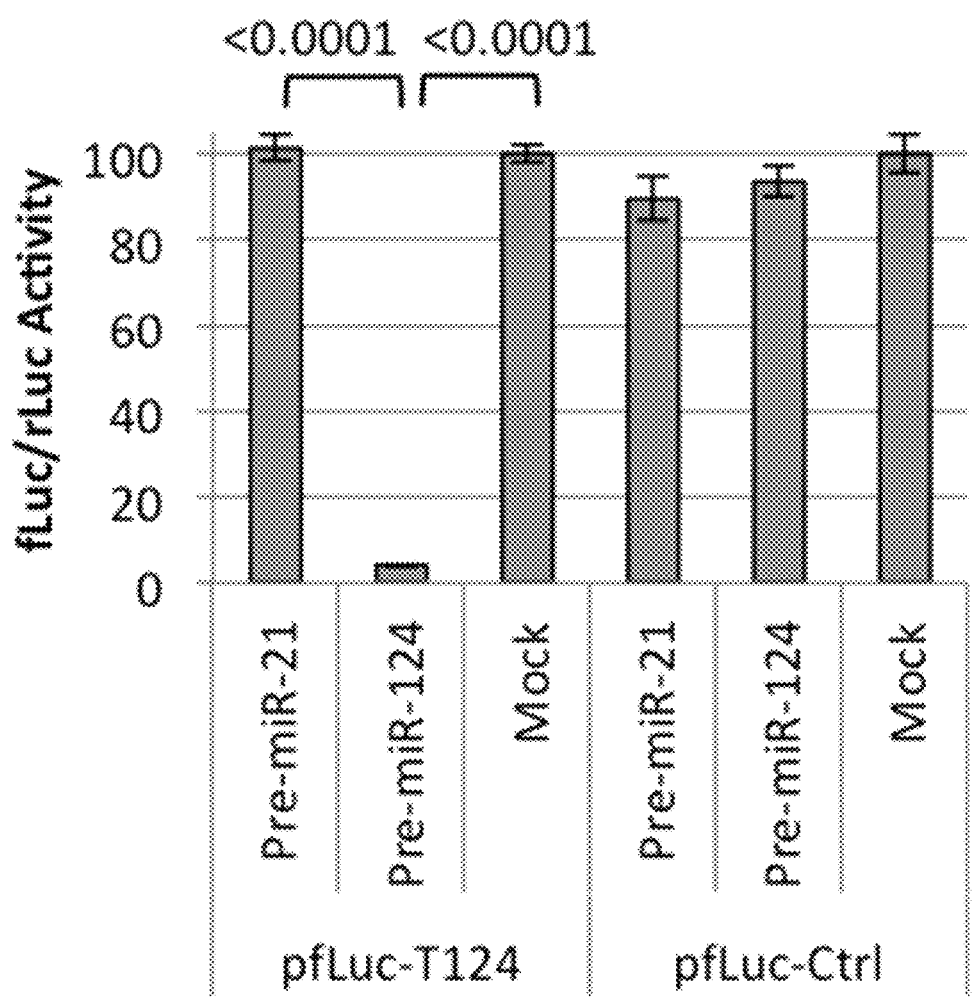

Specification includes a Sequence Listing.

(56) References Cited

FOREIGN PATENT DOCUMENTS

| WO | WO 2008/141151 A2 | 11/2008 |
|---|---|---|
| WO | WO 2008/143875 A1 | 11/2008 |
| WO | WO 2009/111892 A1 | 9/2009 |
| WO | WO 2009/144755 A1 | 12/2009 |
| WO | WO 2009/148488 A2 | 12/2009 |
| WO | WO 2009/150431 A1 | 12/2009 |
| WO | WO 2011/125469 A1 | 10/2011 |
| WO | WO 2011/130749 A2 | 10/2011 |
| WO | WO 2012/006181 A2 | 1/2012 |
| WO | WO 2015/009952 A1 | 1/2015 |
| WO | WO 2015/066042 A1 | 5/2015 |

OTHER PUBLICATIONS

Manservigi, R. et al., 2010, Open Vir. J., vol. 4: pp. 123-156.*
Argnani, R. et al., 2005, Gene Ther., vol. 12: pp. S170-S177.*
Russell, T. et al., J. Virol. Met., 2015, vol. 213: pp. 18-25.*
Russell, T. et al., 2016, vol. PLOS Path., 20 pages.*
U.S. Appl. No. 60/917,752, Cascio et al., filed May 14, 2007.
U.S. Appl. No. 61/847,405, Glorioso et al., filed Jul. 17, 2013.
U.S. Appl. No. 61/562,738, Jonjic, filed Nov. 22, 2011.
U.S. Appl. No. 61/325,137, Glorioso et al., filed Apr. 16, 2010.
Adamiak et al., "Herpes Simplex Virus Type 2 Glycoprotein G is Targeted by the Sulfated Oligo- and Polysaccharide Inhibitors of Virus Attachment to Cells," *Journal of Virology*, 81(24), 13424-13434 (2007).
Aghi et al., "Oncolytic herpes virus with defective ICP6 specifically replicates in quiescent cells with homozygous genetic mutations in p16," *Oncogene*, 27: 4249-4254 (2008).
Akimoto et al., "A new delivery system for 5-fluorouracil using prodrug and converting enzyme," *J. Ophthalmol.*, 86(5): 581-586 (2002).
Amelio et al., "A Chromatin Insulator-Like Element in the Herpes Simplex Virus Type 1 Latency-Associated Transcript Region Binds CCCTC-Binding Factor and Displays Enhancer-Blocking and Silencing Activities," *J. of Virology*, 80(5): 2358-2368 (Mar. 2006).
Anderson et al., "Pseudotyping of Glycoprotein D-Deficient Herpes Simplex Virus Type 1 with Vesicular Stomatitis Virus Glycoprotein G Enable Mutant Virus Attachment and Entry," *Journal of Virology*, 74(5): 2481-2487 (Mar. 2000).
Asano et al., "Humanization of the Bispecific Epidermal Growth Factor Receptor X CD3 Diabody and Its Efficacy as a Potential Clinical Reagent," *Clin. Cancer Res.*, 12(13): 4036-4042 (Jul. 1, 2006).
Assi et al., "Gene Therapy for Brain Tumors: Basic Developments and Clinical Implementation," *Neurosci. Lett.*, 527(2): 71-77 (2012).
Australian Patent Office, Examination Report for Standard Patent Application in Australian Patent Application No. 2014342465 (dated May 26, 2017).
Australian Patent Office, Examination Report for Standard Patent Application in Australian Patent Application No. 2014342465 (dated Aug. 31, 2017).
Australian Patent Office, Examination Report for Standard Patent Application in Australian Patent Application No. 2014342465 (dated Dec. 22, 2017).
Australian Patent Office, International Search Report in International Patent Application No. PCT/US2014/062676 (dated Dec. 23, 2014).
Baek et al., "Bispecific Adapter-Mediated Retargeting of a Receptor-Restricted HSV-1 Vector to CEA-Bearing Tumor Cells," *Molecular Therapy*, 19(3): 507-514 (Mar. 2011).
Bennett et al., "Comparison of safety, delivery, and efficacy of two oncolytic herpes viruses (G207 and NV1020) for peritoneal cancer," *Cancer Gene Therapy*, 9: 935-945 (2002).
Broberg et al., "Immune Response to Herpes Simplex Virus and $\gamma_1$34.5 Deleted HSV Vectors," *Current Gene Therapy*, 5: 523-530 (2005).

Bzik et al., "Nucleotide Sequence of a Region of the Herpes Simplex Virus Type 1 gB Glycoprotein Gene: Mutations Affecting Rate of Virus Entry and Cell Fusion," *Virology*, 37: 185-190 (1984).
Cai et al., "Linker-Insertion Nonsense and Restriction-Site Deletion Mutations of the gB Glycoprotein Gene of Herpes Simplex Virus Type 1," *Journal of Virology*, 61(3): 714-721 (Mar. 1987).
Camacho et al., "Phase 1 clinical trial of anti-CTLA4 human monoclonal antibody CP-675,206 in patients (pts) with advanced solid malignancies," *J. Clin. Oncol.*, 22(145): Abstract No. 2505 (2004) (antibody CP-675206), 4 pp.
Campadelli-Fiume et al., "Rethinking herpes simplex virus: the way to oncolytic agents," *Rev. Med. Virol.*, 21: 213-226 (2011).
Cao et al., "A functional study of miR-124 in the developing neural tube," *Genes & Development*, 21: 531-536 (2007).
Cattaneo et al., "Reprogrammed viruses as cancer therapeutics: targets, armed and shielded," Nature Reviews. Microbiology, 6(7): 529-540 (2008).
Cawood et al., "Use of Tissue-Specific MicroRNA to Control Pathology of Wild-Type Adenovirus without Attenuation of Its Ability to Kill Cancer Cells," *PloS Pathogens*, 5(5): 1-10 (May 2009).
Cheadle et al., "Cloning and expression of the variable regions of mouse myeloma protein MOPC315 in *E. coli*: recovery of active $F_v$ fragments," *Mol. Immunol.*, 29(1): 21-30 (1992).
Cocchi et al., "The Ectodomain of a Novel Member of the Immunoglobulin Subfamily Related to the Poliovirus Receptor Has the Attributes of a Bona Fide Receptor for Herpes Simplex Virus Types 1 and 2 in Human Cells," *Journal of Virology*, 72(12): 9992-10002 (Dec. 1998).
Cocchi et al., "The Herpes Simplex Virus JMP Mutant Enters Receptor-Negative J Cells through a Novel Pathway Independent of the Known Receptors nectin1, HveA, and nectin2," *Journal of Virology*, 78(9): 4720-4729 (May 2004).
Conner et al., "A strategy for systemic delivery of the oncolytic herpes virus HSV1716: redirected tropism by antibody-binding sites incorporated on the virion surface as a glycoprotein D fusion protein," *Gene Therapy*, 15: 1579-1592 (2008).
Connolly et al., "Potential Nectin-1 Binding Site on Herpes Simplex Virus Glycoprotein D," *Journal of Virology*, 79(2): 1282-1295 (Jan. 2005).
Connolly et al., "Structure-Based Analysis of the Herpes Simplex Virus Glycoprotein D Binding Site Present on Herpevirus Entry Mediator HveA (HVEM)," *J. of Virology*, 76(21):10894-10904 (Nov. 2002).
Currier et al., "Efficacy and Safety of the Oncolytic Herpes Simplex Virus rRp450 Alone and Combined With Cyclophosphamide," *Molecular Therapy*, 16(5): 879-885 (2008).
Deluca et al., "Nucleotide Sequences of Herpes Simplex Virus Type 1 (HSV-1) Affecting Virus Entry, Cell Fusion, and Production of Glycoprotein gB (VP7)," *Virology*, 122: 411-423 (1982).
Desai et al., "Incorporation of the Green Fluorescent Protein into the Herpes Simplex Virus Type 1 Capsid," *Journal of Virology*, 72(9): 7563-7568 (Sep. 1998).
Dmitrieva et al., "Choindroitinase ABC I-mediated enhancement of oncolytic virus spread and anti tumor efficacy," *Clin. Cancer Res.*, 17(6): 1362-1372 (2011).
Doronina et al., "Site-Specific Release of Nascent Chains from Ribosomes at a Sense Codon," *Molecular and Cellular Biology*, 28(13): 4227-4239 (2008).
Edge et al., "A let-7 MicroRNA-sensitive Vesicular Stomatitis Virus Demonstrates Tumor-specific Replication," *Molecular Therapy*, 16(8): 1437-1443 (Aug. 2008).
Esko et al., "Animal Cell Mutants Defective in Glycosaminoglycan biosynthesis," *Proc. Natl. Acad. Sci. USA*, 82: 3197-3201 (May 1985).
European Patent Office, European Search Report in European Patent Application No. 17155129 (dated May 30, 2017).
European Patent Office, Office Action in European Patent Application No. 17155129.4, 7 pp. (dated Mar. 27, 2018).
European Patent Office, Office Action in European Patent Application No. 14859119.1, 4 pp. (dated Mar. 27, 2018).
European Patent Office, Supplementary European Search Report in European Patent Application No. 14859119 (dated Apr. 19, 2017).

(56) References Cited

OTHER PUBLICATIONS

Frampton et al., "Equine Herpesvirus 1 Enters Cells by Two Different Pathways, and Infection Requires the Activation of the Cellular Kinase ROCK1," *Journal of Virology*, 81(20): 10879-10889 (2007).
Friedman et al., "Herpes Simplex Virus Oncolytic Therapy for Pediatric Malignancies," *Molecular Therapy*, 17(7): 1125-1135 (2009).
Fu et al., "Construction of an Oncolytic Herpes Simplex Virus That Precisely Targets Hepatocellular Carcinoma Cells," *Mol. Ther.*, 20(2), 339-346 (2012).
Fujioka et al., "Interleukin-18 Protects Mice against Acute Herpes Simplex Virus Type 1 Infection," *J. of Virology*, 73(3): 2401-2409 (1999).
Fuller et al., "Anti-glycoprotein D Antibodies That Permit Adsorption but Block Infection by Herpes Simplex Virus 1 Prevent Virion-cell Fusion at the Cell Surface," *Proc. Natl. Acad. Sci. USA*, 84: 5454-5458 (Aug. 1987).
Fuller et al., "Neutralizing Antibodies Specific for Glycoprotein H of Herpes Simplex Virus Permit Viral Attachment to Cells but Prevent Penetration," *Journal of Virology*, 63(8): 3435-3443 (Aug. 1989).
Gaur et al., "Characterization of MicroRNA Expression Levels and Their Biological Correlates in Human Cancer Cell Lines," *Cancer Res.*, 67(6): 2456-2468 (2007).
Geraghty et al., "Entry of Alphaherpesviruses Mediated by Poliovirus Receptor-Related Protein 1 and Poliovirus Receptor," *Science*, 280: 1618-1620 (Jun. 5, 1998).
Gierasch et al., "Construction and Characterization of Bacterial Artificial Chromosomes Containing HSV-1 Strains 17 and KOS," *J. of Virological Methods*, 135: 197-206 (2006).
Grandi et al., "Design and application of oncolytic HSV vectors for glioblastoma therapy," *Expert Rev. Neurother.*, 9(4): 505-517 (2009).
Grossman et al., "Survival of Patients with Newly Diagnosed Glioblastoma Treated with Radiation and Temozolomide in Research Studies in the United States," *Clinical Cancer Research*, 16: 2443-2449 (2010).
Gubanova et al., "Onkoliticheskiye virusy v terapii gliom," *Molekulyarnaya Biologiya (Mosk)*, 46(6), pp. 874-886 (Nov.-Dec. 2012), ISSN: 0026-8984 (English abstract).
He et al., "Targeting Glioblastoma Stem Cells: Cell Surface Markers," *Current Medicinal Chemistry*, 19: 6050-6055 (2012).
Highlander et al., "Identification of mar Mutations in Herpes Simplex Virus Type 1 Glycoprotein B Which Alter Antigenic Structure and Function in Virus Penetration," *Journal of Virology*, 63(2): 730-738 (Feb. 1989).
Hodi et al., "Improved Survival with Ipilimumab in Patients with Metastatic Melanoma," *The New England Journal of Medicine*, 363(8): 711-723 (2010).
Hong et al., "Ectopic Matrix Metalloproteinase 9 Expression in Human Brain Tumor Cells Enhances Oncolytic HSV Vector Infection," *Gene Ther.*, 17(10): 1200-1205 (2010).
Iorio et al., "microRNA involvement in human cancer," *Carcinogenesis*, 33(6): 1126-1133 (2012).
Ishida et al., "Enhanced cytotoxicity with a novel system combining the paclitaxel-2'-ethylcarbonate prodrug and an Hsv amplicon with an attenuated replication-competent virus, HF10 as a helper virus," *Cancer Letters*, 288: 17-27 (2010).
Israeli Patent Office, Office Action in Israeli Patent Application No. 245312, 4 pp. (dated Feb. 27, 2019).
Jackson et al., "Insertion Mutations in Herpes Simplex Virus 1 Glycoprotein H Reduce Cell Surface Expression, Slow the Rate of Cell Fusion, or Abrogate Functions in Cell Fusion and Viral Entry," *Journal of Virology*, 84(4): 2038-2046 (Feb. 2010).
Japanese Patent Office, Office Action in Japanese Patent Application No. 2016-527106, 16 pp. (dated Jun. 5, 2018).
Japanese Patent Office, Office Action in Japanese Patent Application No. 2016-552209, 11 pp. (dated Sep. 25, 2018).
Kaji et al., "Virus free induction of pluripotency and subsequent excision of reprogramming factors," *Nature*, 458(7239): 771-775 (2009).
Kambara et al., "An Oncolytic HSV-1 Mutant Expressing ICP34.5 under Control of a Nestin Promoter Increases Survival of Animals even when Symptomatic from a Brain Tumor," *Cancer Res.*, 65(7): 2832-2839 (2005).
Karpowicz et al., "E-Cadherin Regulates Neural Stem Cell Self-Renewal," *The Journal of Neuroscience*, 29(12): 3885-3896 (2009).
Karsy et al., "Current Progress on Understanding MicroRNAs in Glioblastoma Multiforme," *Genes & Cancer*, 3(1): 3-15 (2012).
Katoh et al., "Hedgehog signaling, epithelial-to-mesenchymal transition and miRNA (Review)," *International Journal of Molecular Medicine*, 22: 271-275 (2008).
Korean Intellectual Property Office, International Search Report in International Patent Application No. PCT/US2011/032923 (dated Mar. 28, 2012).
Košovský et al., "Herpes Simplex Virus 1 (HSV-1) Strain HSZP Glycoprotein B Gene: Comparison of Mutations among Strains Differing in Virulence," *Virus Genes*, 20(1): 27-33 (2000).
Krisky et al., "Deletion of multiple immediate-early genes from herpes simplex virus reduces cytotoxicity and permits long-term gene expression in neurons," *Gene Therapy*, 5: 1593-1603 (1998).
Krisky et al., "Rapid method for construction of recombinant HSV gene transfer vectors," *Gene Therapy*, 4: 1120-1125 (1997).
Krummenacher et al., "Effects of Herpes Simplex Virus on Structure and Function of Nectin-1/HveC," *Journal of Virology*, 76(5): 2424-2433 (Mar. 2002).
Kuan et al., "Increased Binding Affinity Enhances Targeting of Glioma Xenografts by EGFRVIII-Specific scFv," *Int. J. Cancer*, 88: 962-969 (2000).
Kumar et al., "Impaired microRNA processing enhances cellular transformation and tumorigenesis," *Nature Genetics*, 39(5): 673-677 (2007).
Kwon et al., "Soluble V Domain of Nectin-1/HveC Enables Entry of Herpes Simplex Virus Type 1 (HSV-1) into HSV-Resistant Cells by Binding to Viral Glycoprotein D," *Journal of Virology*, 80(1): 138-148 (Jan. 2006).
Lavon et al., "Gliomas display a microRNA expression profile reminiscent of neural precursor cells," *Neuro-Oncology*, 12(5): 422-433 (2010).
Lee et al., "MicroRNA Regulation of Oncolytic Herpes Simplex Virus-1 for Selective Killing of Prostate Cancer Cells," *Clin. Cancer Res.*, 15(16): 5126-5135 (Aug. 15, 2009).
Li et al, "Identification of Functional Domains in Herpes Simplex Virus 2 Glycoprotein B," *J. of Virology*, pp. 3792-3800 (Apr. 2006).
Ligas et al., "A Herpes Simplex Virus Mutant in Which Glycoprotein D Sequences Are Replaced by β-Galactosidase Sequences Binds to but Is Unable to Penetrate into Cells," *J. of Virology*, 62(5): 1486-1494 (May 1988).
Lilley et al., "Multiple Immediate-Early Gene-Deficient Herpes Simplex Virus Vectors Allowing Efficient Gene Delivery to Neurons in Culture and Widespread Gene Delivery to the Central Nervous System In Vivo," *J. of Virology*, 75:9: 4343-4356 (May 2001).
Ma et al., "A novel HBV antisense RNA gene delivery system targeting hepatocellular carcinoma," *World J. of Gastro*, 9(3), 463-467 (2003).
MacDonald et al., "Genome Sequence of Herpes Simplex Virus 1 Strain KOS," *Journal of Virology*, 86(11): 6371-6372 (Jun. 2012).
Mammoto et al., "Role of Collagen Matrix in Tumor Angiogenesis and Glioblastoma Multiforme Progression," *The American Journal of Pathology*, 183(4): 1293-1305 (2013).
Manickan et al., "Genetic immunization against herpes simplex virus. Protection is mediated by CD4+ T lymphocites," *The Journal of Immunology*, 155: 259-265 (1995).
Markert et al., "Conditionally replicating herpes simplex virus mutant, G207 for the treatment of malignant glioma: results of a phase I trial," *Gene Therapy*, 7: 867-874 (2000).
Mazzacurati et al., "Use of miRNA Response Sequences to Block Off-target Replication and Increase the Safety of an Unattenuated, Glioblastoma-targeted Oncolytic HSV," *Molecular Therapy*, 23(1): 99-107 (2015).

(56) References Cited

OTHER PUBLICATIONS

McKee et al., "Degradation of Fibrillar Collagen in a Human Melanoma Xenograft improves the Efficacy of an Oncolytic Herpes Simplex Virus Vector," Cancer Research, 66(5): 2509-2513 (2006).
Menotti et al., "Construction of a Fully Retargeted Herpes Simplex Virus 1 Recombinant Capable of Entering Cells Solely via Human Epidermal Growth Factor Receptor 2," Journal of Virology, 82(20): 10153-10161 (Oct. 2008).
Menotti et al., "Inhibition of Human Tumor Growth in Mice by an Oncolytic Herpes Simplex Virus Designed to Target Solely HER-2-positive Cells," PNAS, 106(22): 9039-9044 (Jun. 2, 2009).
Miao et al., "Use of miRNA Response Sequences to Block Off-target Replication and Increase the Safety of an Unattenuated, Glioblastoma-targeted Oncolytic HSV," Oncogene, 34(5): 558-567 (2015).
Miest et al., "New viruses for cancer therapy: meeting clinical needs," Nature Reviews. Microbiology, 12(1): 23-34 (2014).
Miller et al., "Development of a Syngenic Murine B16 Cell Line-Derived Melanoma Susceptible to Destruction by Neuroattenuated HSV-1," Molecular Therapy, 3(2): 160-168 (Feb. 2001).
Milne et al., "Glycoprotein D Receptor-Dependent, Low-pH-Independent Endocytic Entry of Herpes Simplex Virus Type 1," Journal of Virology, 79(11): 6655-6663 (Jun. 2005).
Mohyeldin et al., "Gene and Viral Therapy for Glioblastoma A Review of Clinical Trials and Future Directions," The Cancer Journal, 18(1): 82-88 (2012).
Mok et al., "Matrix Metalloproteinases-1 and -8 Improve the Distribution and Efficacy of an Oncolytic Virus," Cancer Res., 67(22): 10664-10668 (2007).
Montgomery et al., "Herpes Simplex Virus-1 Entry into Cells Mediated by a Novel Member of the TNF/NGF Receptor Family," Cell, 87: 427-436 (Nov. 1, 1996).
Muggeridge, "Characterization of Cell-cell Fusion Mediated by Herpes Simplex Virus 2 glycoproteins gB, gD, gH and gL in Transfected Cells," Journal of General Virology, 81: 2017-2027 (2000).
Mullokandov et al. "High-throughput assessment of microRNA activity and function using microRNA sensor and decoy libraries," Nature Methods, 9, pp. 840-846 (2012).
Nakano et al., "Mechanism of HSV infection through soluble adapter-mediated virus bridging to the EGF receptor," Virology, 413: 12-18 (2011).
Navaratnarajah et al., "Targeted Entry of Enveloped Viruses: Measles and Herpes Simplex Virus I," Curr. Opin. Virol., 2(1): 43-49 (2012).
NCBI, "Chain A, Glycoprotein B From Herpes Simplex Virus Type 1, A549t Rate-of-entry Mutant, Low-ph," Database Entrez-Nucleotide, Accession No. 4L1 R_A (Jun. 26, 2013), retrieved May 19, 2015.
NCBI, "glycoprotein B [Human herpesvirus 1]," Database Entrez-Nucleotide, Accession No. AAF70301 (May 16, 2000), retrieved May 19, 2015.
NCBI, "glycoprotein B [Human herpesvirus 1]," Database Entrez-Nucleotide, Accession No. AAA91805 (Mar. 8, 1996), retrieved May 19, 2015.
NCBI, "glycoprotein B [Human herpesvirus 2]," Database Entrez-Nucleotide, Accession No. ABU45427 (Nov. 29, 2007), retrieved May 19, 2015.
NCBI, "Herpes Simplex Virus Type 1 Gene for Glycoprotein gH," Database GenBank Accession No. X03896 (Apr. 18, 2005), retrieved Oct. 15, 2012.
NCBI, "Human Herpesvirus 1 Complete Genome," Databse GenBank Accession No. X14112 (Oct. 23, 2008), retrieved Oct. 15, 2012.
NCBI, "Human Herpesvirus 1 Strain Kos Glycoprotein B Gene," Database GenBank Accession No. AF311740 (Jan. 24, 2001), retrieved Oct. 15, 2012.
Nduom et al., "Glioblastoma Cancer Stem-like Cells—Implications for Pathogenesis and Treatment," Cancer J., 18(1): 100-106 (2012).
Nicola et al., "Cellular and Viral Requirements for Rapid Endocytic Entry of Herpes Simplex Virus," Journal of Virology, 78(14): 7508-7517 (Jul. 2004).
Nicola et al., "Roles for Endocytosis and Low pH in Herpes Simplex Virus Entry into HeLa and Chinese Hamster Ovary Cells," Journal of Virology, 77(9): 5324-5332 (May 2003).
Ocana et al., "A new regulatory loop in cancer-cell invasion," European Molecular Biology Organization, 9(6): 521-522 (2008).
Omidfar et al., "Production and Characterization of a New Antibody Specific for the Mutant EGF Receptor, EGFRvIII, in Camelus bactrianus," Tumor Biology, 25:179-187 (2004).
Omidfar et al., "Production of a Novel Camel Single-Domain Antibody Specific for the Type III Mutant EGFR," Tumor Biology, 25: 296-305 (2004).
Opalinska et al., "Nucleic-Acid Therapeutics: Basic Principles and Recent Applications," Nature Reviews, 1, pp. 503-514 (2002).
Parker et al., "Oncolytic Viral Therapy of Malignant Glioma," Neurotherapeutics: The Journal of the American Society for Experimental NeuroTherapeutics, 6: 558-569 (2009).
Patriarca et al., "Epithelial cell adhesion molecule expression (CD326) in cancer: A short review," Cancer Treatment Reviews, 38: 68-75 (2012).
Payne et al., "The Pathobiology of Collagens in Glioma," Mol. Cancer Res., 11: 1129-1140 (2013).
Pertel et al., "Cell Fusion Induced by Herpes Simplex Virus Glycoproteins gB, gD, and gH-gL Requires a gD Receptor but Not Necessarily Heparan Sulfate," Virology, 279: 313-324 (2001).
Raag et al., "Single-chain Fvs," FASEB, 9(1):73-80 (1995).
Rauch et al., "Mutations in Herpes Simplex Virus Glycoprotein D Distinguish Entry of Free Virus from Cell-Cell Spread," Journal of Virology, 74(24): 11437-11446 (Dec. 2000).
Riddick et al., "Integration and analysis of genome-scale data from gliomas," Nature Reviews—Neurology, 7: 439-450 (2011).
Russian Patent Office, Office Action in Russian Patent Application No. 2016120618, 10 pp. (dated May 22, 2018).
Russian Patent Office, Office Action in Russian Patent Application No. 2016101106, 11 pp. (dated Jul. 11, 2018).
Saharkhiz-Langroodi et al., "Identification of the Fusion-from-without Determinants of Herpes Simplex Virus Type 1 Glycoprotein B," Virology, 227, 153-159 (1997).
Schaffer et al., "Temperature-Sensitive Mutants of Herpes Simplex Virus Type 1: Isolation, Complementation and Partial Characterization," Virology, 52: 57-71 (1973).
Sethi et al., "Protection of Mice from Fatal Herpes Simplex Virus Type 1 Infection by Adoptive Transfer of Cloned Virus-specific and H-2-restricted Cytotoxic T Lymphocytes," J. Gen. Virol., 64: 443-447 (1983).
Shi et al., "hsa-mir-181a and hsa-mir-181b function as tumor suppressors in human glioma cells," Brain Research, 1236: 185-193 (2008).
Shogan et al., "Virucidal Activity of a GT-Rich Oligonucleotide against Herpes Simplex Virus Mediated by Glycoprotein B," Journal of Virology, 80(10): 4740-4747 (May 2006).
Silber et al., "miR-124 and miR-137 inhibit proliferation of glioblastoma multiforme cells and induce differentiation of brain tumor stem cells," BMC Medicine, 6(14): 1-17 (2008).
Slavuljica et al., "Recombinant mouse cytomegalovirus expressing a ligand for the NKG2d receptor is attenuated and has improved vaccine properties," J. Clin. Invest., 120(12): 4532-4545 (Dec. 2010).
Smith, "Relationship Between the Envelope and the Infectivity of Herpes Simplex Virus," Herpes Virus Envelopes, 814-816 (1964).
Struyf et al., "Mutations in the N-Terminal Domains of Nectin-1 and Nectin-2 Reveal Differences in Requirements for Entry of Various Alphaherpesviruses and for Nectin-Nectin Interactions," Journal of Virology, 76(24): 12940-12950 (Dec. 2002).
Szymczak et al., "Development of 2A peptide-based strategies in the design of multicistronic vectors," Expert Opin. Biol. Ther., 5(5): 627-638 (2005).
The International Bureau of WIPO, International Preliminary Report on Patentability issued by the International Searching Authority for International Patent Application No. PCT/US2014/062676 (dated May 3, 2016).

(56) References Cited

OTHER PUBLICATIONS

The International Bureau of WIPO, International Preliminary Report on Patentability issued by the International Searching Authority for International Patent Application No. PCT/US2011/032923, 8 pp. (dated Oct. 16, 2012).
Thomas et al., "Equine Herpesvirus 1 Gene 12 Can Substitute for vmw65 in the Growth of Herpes Simplex Virus (HSV) Type 1, Allowing the Generation of Optimized Cell Lines for the Propagation of HSV Vectors with Multiple Immediate-Early Gene Defects," *J. of Virology*, 73(9): 7399-7409 (Sep. 1999).
Tischer et al., "Two-step Red-mediated recombination for versatile high-efficiency markerless DNA manipulation in *Escherichia coli*," *Bio Techniques*, 40(2): 191-196 (2006).
Todo, "Oncolytic Virus Therapy Using Genetically Engineered Herpes Simplex Viruses," *Human Cell*, 15(3): 151-159 (2002).
Topalian et al., "Safety, Activity, and Immune Correlates of Anti—PD-1 Antibody in Cancer," *The New England Journal of Medicine*, 366(26): 2443-2454 (2012).
Tsvitov et al., "Characterization of Soluble Glycoprotein D-mediated Herpes Simplex Virus Type 1 Infection," *Virology*, 360: 477-491 (2007).
Turner et al., "Glycoproteins gB, gD, and gHgL of Herpes Simplex Virus Type 1 Are Necessary and Sufficient to Mediate Membrane Fusion in a Cos Cell Transfection System," *Journal of Virology*, 72(1): 873-875 (Jan. 1998).
U.S. Patent Office, International Search Report in International Patent Application No. PCT/US2017/037531, 4 pp. (dated Sep. 29, 2017).
U.S. Patent Office, Written Opinion in International Patent Application No. PCT/US2017/037531, 4 pp. (dated Sep. 29, 2017).
Uchida et al., "A Double Mutation in Glycoprotein gB Compensates for Ineffective gD-Dependent Initiation of Herpes Simplex Virus Type 1 Infection," *Journal of Virology*, 84(23): 12200-12209 (Dec. 2010).
Uchida et al., "Co-engineering of HSV-1 gB and gD Enables Efficient Retargeted Infection," *29th Annual Meeting of the American Society for Virology*, slides of oral presentation, 38 pages, Bozeman, MT (Jul. 17-21, 2010).
Uchida et al., "Co-engineering of HSV-1 Glycoproteins B and D Enables Highly Efficient Retargeted Infection," *29th Annual Meeting of the American Society for Virology*, abstract, 1 page, Bozeman, MT (Jul. 17-21, 2010).
Uchida et al., "Effective Treatment of an Orthotopic Xenograft Model of Human Glioblastoma Using an EGFR-retargeted Oncolytic Herpes Simplex Virus," *Molecular Therapy*, 21(3): 561-569 (2013).
Uchida et al., "Fully Retargeted HSV-1 Infection Directed by Re-Engineered Glycoprotein D (gD) Is Augmented by Hyperactive gB Mutations," *Molecular Therapy*, 18(Supp. 1): S249, Abstract 640 (May 2010).
Uchida et al., "Generation of Herpesvirus Entry Mediator (HVEM)-Restricted Herpes Simplex Virus Type 1 Mutant Viruses: Resistance of HVEM-Expressing Cells and Identification of Mutations That Rescue Nectin-1 Recognition," *Journal of Virology*, 83(7): 2951-2961 (Apr. 2009).
Uchida et al., "Hyperactive gB Mutations Augment Fully Retargeted HSV Infection," *13th Annual Meeting of the American Society of Gene & Cell Therapy*, slides of oral presentation, 34 pages, Washington, DC (May 19-22, 2010).
Uchida et al., "Hyperactive gB Mutations Augment Fully Retargeted HSV Infection," *35th Annual International Herpes Virus Workshop*, poster presentation, 1 page, Salt Lake City, UT (Jul. 24-29, 2010).
Uchida et al., "Hyperactive Glycoprotein B Mutations Augment Fully Retargeted HSV Infection," *35th Annual International Herpes Virus Workshop*, abstract, 1 page, Salt Lake City, UT (Jul. 24-29, 2010).
Uchida et al., "Identification of Mutations in HSV-1 Envelope Glycoprotein B That Enhance Retargeted Infection," *Proceedings of the American Association for Cancer Research*, 51: 139, Abstract 584 (Apr. 2010).

Uchida et al., "Novel Mutations in gB and gH Circumvent the Requirement for Known gD Receptors in Herpes Simplex Virus 1 Entry and Cell-to-Cell Spread," *Journal of Virology*, 87(3): 1430-1442 (Feb. 2013).
Uchida et al., "Hyperactive Glycoprotein B (gB) Mutations Augment Fully Retargeted Herpes Simplex Virus (HSV) Infection," *101st Annual Meeting of the American Association for Cancer Research*, poster presentation, 1 page, Washington, DC (Apr. 18, 2010).
Ushijima et al., "Determination and Analysis of the DNA Sequence of Highly Attenuated Herpes Simplex Virus Type 1 Mutant HF10, a Potential Oncolytic Virus," *Microbes and Infection*, 9: 142-149 (2007).
Varghese et al., "Oncolytic herpes simplex virus vectors for cancer virotherapy," *Cancer Gene Therapy*, 9(12): 967-978 (2002).
Verhaak et al., "Integrated Genomic Analysis Identifies Clinically Relevant Subtypes of Glioblastoma Characterized by Abnormalities in PDGFRA, IDH1, EGFR, and NF1," *Cancer Cell*, 17: 98-110 (2010).
Visvanathan et al., "The microRNA miR-124 antagonizes the anti-neural REST/SCP1 pathway during embryonic CNS development," *Genes & Development*, 21: 744-749 (2007).
Voeks et al., "Gene therapy for prostate cancer delivered by ovine adenovirus and mediated by purine nucleoside phosphorylase and fludarabine in mouse models," *Gene Therapy*, 9(12): 759-768 (2002).
Wakimoto et al., "Effects of innate immunity on herpes simplex virus and its ability to kill tumor cells," *Gene Therapy*, 10: 983-990 (2003).
Warner et al., "A Cell Surface Protein with Herpesvirus Entry Activity (HveB) Confers Susceptibility to Infection by Mutants of Herpes Simplex Virus Type 1, Herpes Simples Virus Type 2, and Pseudorabies Virus," *Virology*, 246: 179-189 (1998).
Wikstrand et al., "Monoclonal Antibodies against EGFRvIII Are Tumor Specific and React with Breast and Lung Carcinomas and Malignant Gliomas," Cancer Research, 55: 3140-3148 (Jul. 15, 1995).
Wong et al., "Targeted Oncolytic Herpes Simplex Viruses for Aggressive Cancers," *Current Pharmaceutical Biotechnology*, 13: 1786-1794 (2012).
Xia et al., "Loss of Brain-enriched miR-124 MicroRNA Enhances Stem-like Traits and Invasiveness of Glioma Cells," *The Journal of Biological Chemistry*, 287(13): 9962-9971 (2012).
Yan et al., "Effective small RNA destruction by the expression of a short tandem target mimic in *Arabidopsis*," *The Plant Cell*, 24, pp. 415-427 (2012).
Yin et al., "The treatment of glioblastomas: A systematic update on clinical Phase III Trials," *Critical Reviews in Oncology/Hematology*, 87: 265-282 (2013).
Yun, "Overcoming the extracellular matrix barrier to improve intratumoral spread and therapeutic potential of oncolytic virotherapy," *Current Opinion in Molecular Therapeutics*, 10(4): 356-361 (2008).
Zhang et al., "Abstract 3669: IDH mutant glial cell resistance to natural killer cell cytotoxicity," *Cancer Research*, 74, 3669 (Oct. 1, 2014).
Zhang et al., "MicroRNA-128 inhibits glioma cells proliferation by targeting transcription factor E2F3a," *J. Mol. Med.*, 87: 43-51 (2009).
Zhou et al., "Construction and Properties of a Herpes Simplex Virus 1 Designed to Enter Cells Solely via the IL-13α2 Receptor," *PNAS*, 103(14): 5508-5513 (Apr. 4, 2006).
Liu et al., "ICP34.5 deleted herpes simplex virus with enhanced oncolytic, immune stimulating, and anti-tumor properties," *Gene Therapy*, 10(4): 292-303 (2003).
Chen et al., "Neither LAT nor Open Reading Frame P Mutations Increase Expression of Spliced or Intron-Containing ICP0 Transcripts in Mouse Ganglia Latently Infected with Herpes Simplex Virus", *Journal of Virology* 76(10): 4764-4772 (2002).
Extended European Search Report dated Dec. 22, 2020 in EP Application No. 20184441.2.
Jenkins et al., "Deletion of the herpes simplex 1 internal repeat sequences affects pathogenicity in the mouse," *Front. Biosoi*, 1: a59-68 (1996).

(56) References Cited

OTHER PUBLICATIONS

Junejo et al., "Deletions and duplication in internal inverted repeat sequence of long region/unique sequence of long region (IRL/UL) of herpes simplex virus type-1 (HSV-1) genome are not evidently associated with intracranial and foot-pad pathogenicity in mouse model," *J. Pak Med. Assoc*, 45(40): 95-98 (1995).
Stamenkovich, "Extracellular matrix remodeling: the role of matrix metalloproteinases," *J. Pathology*, 200: 448-464 (2003).
Tocchi et al., "Functional interactions between matrix metalloproteinases and glycosaminoglycans," *The FEBS Journal*, 280: 2332-2341 (2013).
Wollman et al., "Oncolytic Virus Therapy of Glioblastoma Mulitform—Concepts and Candidates," *Cancer J.*, 18(1): 69-81 (2012).
Banerjee et al., "Herpex Simplex Virus: The Hostile Guest that Takes Over Your Home", *Frontiers in Microbiology*, 11: 733, pp. 1-18 (2020).
U.S. Appl. No. 15/032,958, filed Apr. 28, 2016.
U.S. Appl. No. 15/204,350, filed Jul. 7, 2016.
U.S. Appl. No. 15/616,585, filed Jun. 7, 2017.
U.S. Appl. No. 16/190,370, filed Nov. 14, 2018.
U.S. Appl. No. 16/191,141, filed Nov. 14, 2018.
U.S. Appl. No. 16/746,145, filed Jan. 17, 2020.
Todo, "Oncolytic virus therapy using genetically engineered herpes simplex viruses", *Frontiers in Bioscience* (*Landmark Ed.*), 13(6): 2060-2064 (2008).

\* cited by examiner

Most Similar Starting Volume

ONCOLYTIC HSV VECTOR

CROSS-REFERENCE TO RELATED APPLICATIONS

This patent application is a continuation application of U.S. patent application Ser. No. 16/746,145, filed Jan. 17, 2020, now abandoned, which claims priority to U.S. patent application Ser. No. 16/191,141, filed Nov. 14, 2018, now U.S. Pat. No. 10,576,115, which claims priority to U.S. patent application Ser. No. 15/616,585, filed Jun. 7, 2017, now U.S. Pat. No. 10,172,893, which claims priority to U.S. patent application Ser. No. 15/032,958, filed Apr. 28, 2016, now U.S. Pat. No. 10,201,575, which claims priority to International Patent Application No. PCT/US2014/062676, filed Oct. 28, 2014, which claims priority to U.S. Provisional Patent Application No. 61/896,497, filed Oct. 28, 2013, each of which are incorporated by reference herein in their entirety.

STATEMENT REGARDING FEDERALLY SPONSORED RESEARCH AND DEVELOPMENT

This invention was made with Government support under Grant Numbers CA119298, CA163205, CA175052, NS040923, and DK044935 awarded by the National Institutes of Health. The Government has certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 4,069 Byte ASCII (Text) file named "750428 ST.25.TXT," created on Aug. 4, 2020.

BACKGROUND OF THE INVENTION

Glioblastoma multiforme (GBM) is a uniformly fatal disease despite the application of available combination therapies. Preclinical studies suggest that replication competent viruses including oncolytic HSV ("oHSV") vectors, represent a promising therapeutic alternative but treatment efficacy in patient trials has been limited. Achieving vector safety has relied on attenuating vector mutations that can also compromise lytic replication in tumor cells.

SUMMARY OF THE INVENTION

The present invention provides an oHSV capable of tumor-selective vector replication without attenuation by combining vector retargeting to tumor-associated cell surface receptors with inhibition of vector replication by a cellular microRNA ("miR") that is highly expressed in normal brain but virtually absent in tumor cells. miR-responsive elements prevent vector pathogenesis in the brains of nude mice without impeding lytic vector replication in primary tumor cells in vitro or in a xenogeneic brain tumor model. This new vector design should provide a safer and more effective vector platform and can be further developed for application to patient tumors.

BRIEF DESCRIPTION OF THE SEVERAL VIEWS OF THE DRAWING(S)

FIG. 1 presents data from the results of experiments concerning the effectiveness and specificity of the T124 element. Firefly luciferase (fLuc) expression plasmids containing T124 (pfLuc-T124) or a control sequence (pfLuc-Ctrl) in the 3'UTR were co-transfected with a renilla luciferase (prLuc) internal control plasmid into HEK293AD cells transfected 24 h earlier with synthetic pre-miR-124 or pre-miR-21. Luciferase activities were measured 48 h later. The results are shown as the means±standard deviations from three determinations for fLuc activity normalized to rLuc activity. Statistically significant differences between pairs are indicated by brackets underneath the corresponding P values (unpaired t test).

FIGS. 2A-2D present data from the results of experiments concerning virus replication in glioma cells. (A) Vector diagrams. The parental KOS-37 BAC contains loxP-flanked BAC, chloramphenicol-resistance and lacZ sequences ("BAC") between the viral UL37 and UL38 genes (Gierasch et al., 2006). Modifications to generate KGBAC and KG4:T124BAC are illustrated, as follows: gB:NT, virus entry-enhancing double mutation in the gB gene; gC-eGFP, fusion of the complete gC ORF to GFP via a 2A peptide sequence; ΔJoint, deletion of the complete internal repeat region, including one copy of the ICP4 gene; ICP4: T124, insertion of T124 in the 3'UTR of the remaining ICP4 gene. UL, unique long segment of the viral genome; US, unique short segment. (B) Effect of T124 on virus replication in patient-derived glioma cells in culture. Gli68 and GBM30 cells were infected with KG or KG4:T124 viruses in triplicate at an MOI of 0.01. At the indicated time points post infection, cell lysates and supernatants were collected and titered on U2OS cells. Values are means±standard deviation. (C) MiR-124 expression in LV124-infected Gli68 cells. Cells were infected at 5 cfu/cell, selected the following day for 3 days in puromycin-containing media, and harvested for total RNA extraction. Control RNAs were from uninfected Gli68 and U2OS cells. miR-124 levels were determined in triplicate by qRT-PCR and normalized to RNU43 levels. Shown is the fold increase ±standard deviation relative to U2OS cells. P<0.05 for all pairs (unpaired t test). (D) KG and KG4:T124 virus replication in miR-124-transduced and control GBM30 and Gli68 cells. Cells were infected with LV124 or LV137R at 5 cfu/cell, selected with puromycin for 3 d, and super-infected at MOIs of 0.01 with KG or KG4:T124. Infectious HSV in combined cell lysates and supernatants collected 72 and 96 h later was titered on U2OS cells. Results are the mean values±standard deviation from triplicate HSV infections. Brackets indicate significantly different pairs with the corresponding P values shown (unpaired t test).

Figure 3:
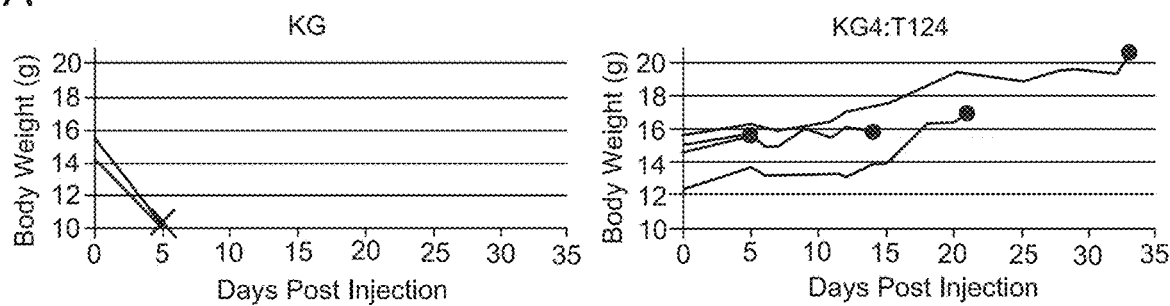
Figure 3:
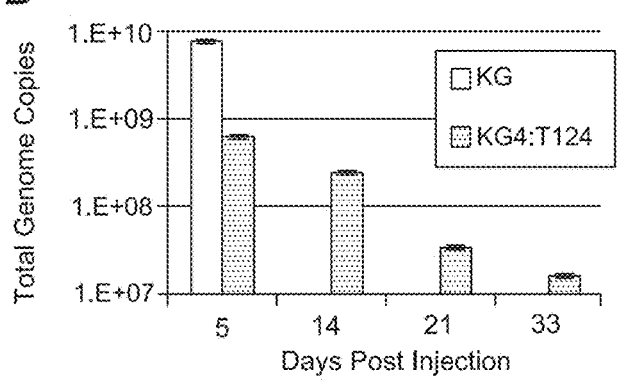
Figure 3:
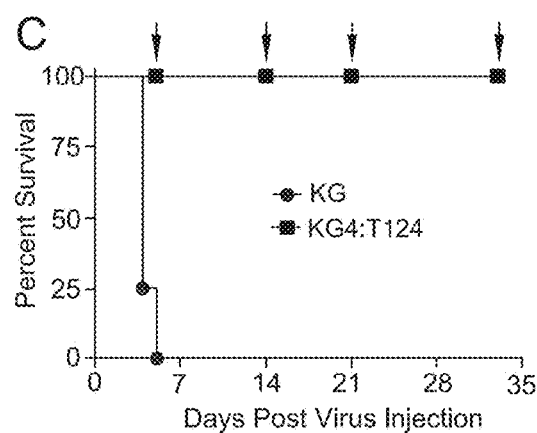

FIGS. 3A-3C present data from the results of experiments concerning KG4:T124 virus replication and toxicity in nude mouse brains. 4.8×10⁹ genome copies of KG or KG4:T124 were intracranially injected into 4 BALB/c nude mice each (n=4/group). (A) Animal weights over time post vector injection. Left, KG-injected animals; X, animal death. Right, KG4:T124-injected mice; filled circles, animal sacrifice. (B) Total viral genome copies over time in mouse brains following vector injection. Brains from single KG4:T124-injected mice sacrificed on days 5, 14, 21 and 33 post vector injection and the last surviving animal from the KG-injected group euthanized on day 5 with severe symptoms of disease were collected, DNA was isolated, and the total numbers of viral vector genomes per brain were determined by qPCR. (C) Kaplan-Meier survival plot of the animals in this experiment. Arrows indicate the days of sacrifice of single animals from the KG4:T124-injected group. P=0.0058, log-rank test.

Figure 4A:
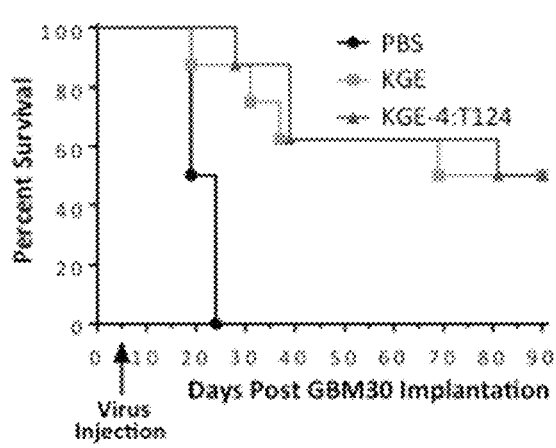
Figure 4B:
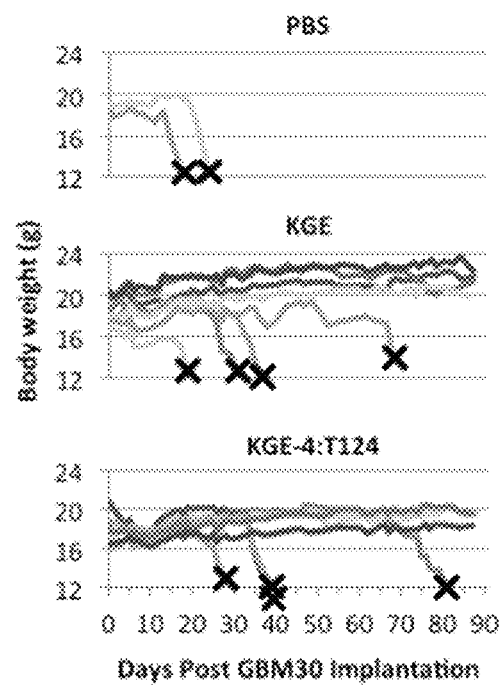

FIGS. 4A-4B present data from the results of experiments concerning EGFR-retargeted miR-124-sensitive HSV vector treatment of a nude mouse model of human glioblastoma. Triturated GBM30 cells were implanted intracranially and 5 days later, PBS or $1.8 \times 10^8$ gc of KGE or KGE-4:T124 virus were injected at the same coordinates. (A) Kaplan-Meier survival plot. Log-rank statistics: KGE vs. PBS, P=0.0188; KGE-4:T124 vs. PBS, P=0.0009; KGE vs. KGE-4:T124, P=0.8327. (B) Animal weights over time post tumor-cell implantation. X, animal death or euthanasia.

FIGS. 5A-5D present data demonstrating that KMMP9 mediates overexpression of enzymatically active MMP9. (A) Structure of KMMP9 and KGw. (B) Western blot analysis of cell lysates of Vero cells infected with either KMMP9, KGw, or KG (MOI=0.1). β-tubulin and HSV glycoprotein B were visualized as cellular and viral loading controls, respectively. Primary GBM cell lines (C) or Vero cells (D) were infected with KGw or KMMP9 at MOI=1. Cell lysate and supernatant were collected 24 h after infection and were combined (C) or loaded separately (D) on a 10% polyacrylamide/0.1% gelatin gel. After electrophoresis, the gel was incubated overnight at 37° C., stained with 0.05% Coomassie Blue and destained, and the image was recorded. Abbreviations: M, KMMP9; G, KGw; KG, control virus; un., uninfected; gB, glycoprotein B; Sup., supernatant.

Figure 6A:
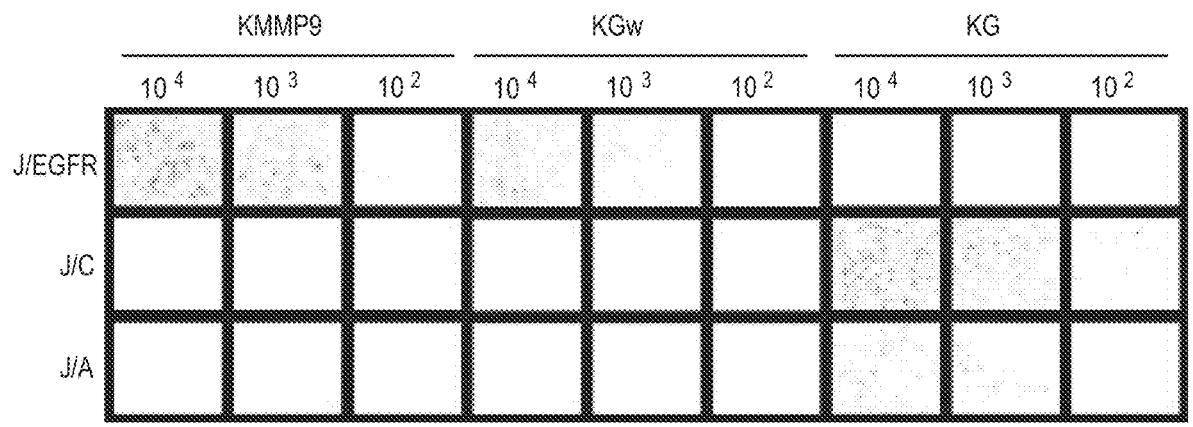
Figure 6B:
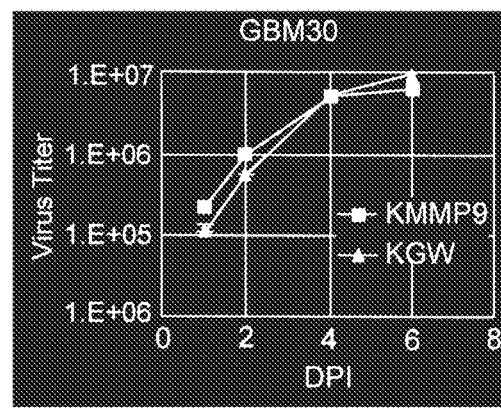
Figure 6C:
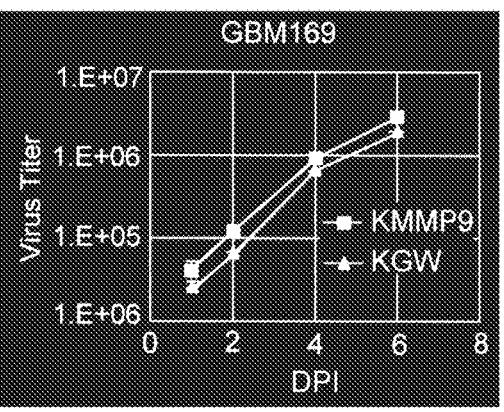

FIGS. 6A-6C present data demonstrating that KMMP9 and KGw exhibit comparable cell entry and growth patterns. (A) Cells listed to the left of the panel were infected with virus at the multiplicities in gc/cell listed above the panels. After 6 hours cells were fixed and immunostained for ICP4. (B) GBM30 and (C) GBM169 cells were dissociated and infected with KMMP9 or KGw at 200 gc/cell. Cell lysates were collected at 1, 2, 4, and 6 dpi and viral genome copy titers were determined by qPCR. No significant differences were observed between the two viruses in either host cell line (GBM30: P=0.20; GBM169: P=0.11).

Figure 7A:
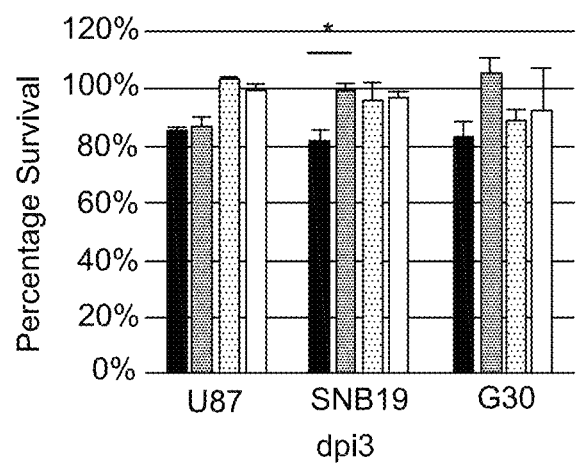
Figure 7B:
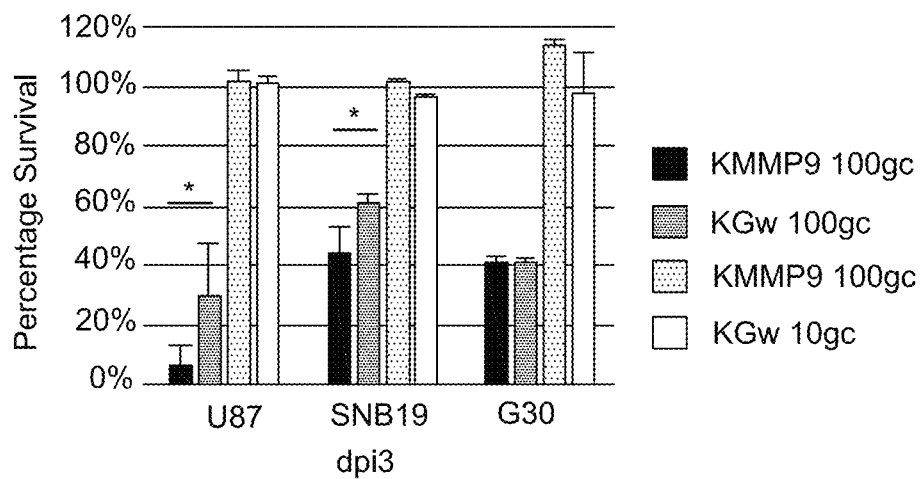

FIGS. 7A-7B present data demonstrating that KMMP9 shows similar or better tumor cell killing in comparison with KGw in vitro. U87, SNB19 or GBM30 cells were infected at 10 or 100 gc/cell for 3 or 7 days. Percentage cell survival relative to uninfected cells was determined by MTT assay (n=3; asterisk: P<0.05, unpaired student t-test).

FIGS. 8A-8E present data demonstrating that MMP9 improves infectivity of oHSV in spheroids. GBM30 cells were grown in suspension and infected with $1 \times 10^3$ pfu of either KMMP9 or KGw. Green fluorescence from the gC-T2a-eGFP cassette in both vectors was visualized daily at 2-6 dpi in whole-mount spheroids. (A) Representative images at 3 and 5 dpi. (B) Averaged quantification of eGFP signal in 6 spheroids per vector demonstrated an approximately 2-fold infectivity increase of KMMP9 over KGw (P=0.006). (C-E) Two groups of GBM30 spheroids were infected with KMMP9 or KGw at $4 \times 10^7$ genome copies per spheroid. Spheroids were fixed, stained with DAPI, and Z section confocal images were recorded at intervals of 5 μm. Panel (C) shows 2 representative spheroids each from the KMMP9 and KGw groups after 3D reconstruction from 0 μm to 150 μm. Panel (D) shows Z-sections of 2 spheroids from each group at Z=100 μm. (E) Each spheroid was divided into 5 segments in terms of depth on the Z axis (from bottom up: 0-20 μm, 25-50 μm, 55-80 μm, 85-100 μm, 105-120 μm, and 125-140 μm). Relative signal intensity in each segment of the spheroid was calculated by averaging eGFP signal divided by DAPI signal. n=7; asterisk: P<0.05.

Figure 9:
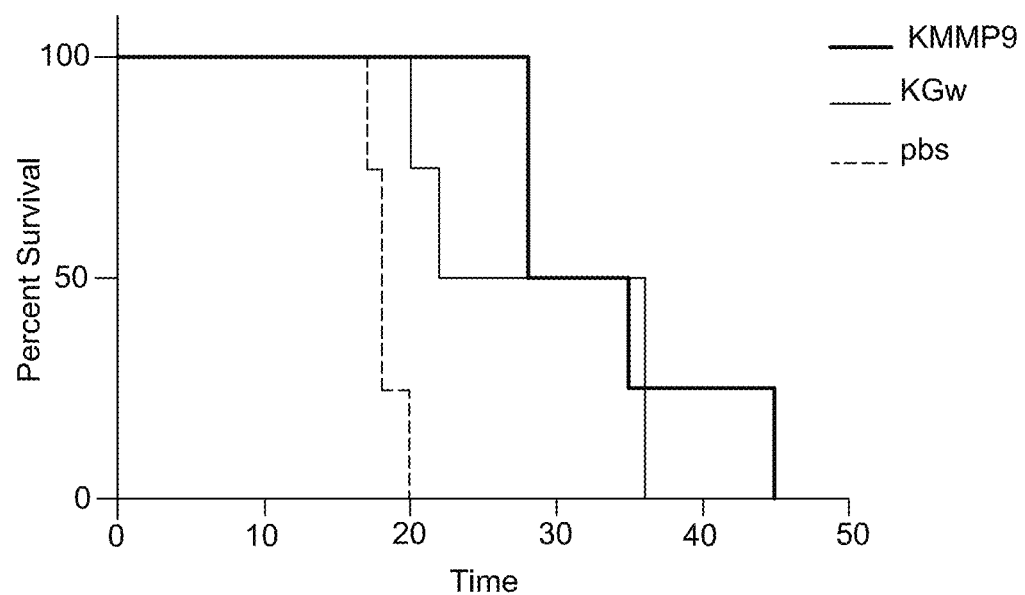

FIG. 9 presents data concerning KMMP9 treatment of a nude mouse model of GBM. GBM30 cells were implanted intracranially and KMMP9, KGw or PBS were injected 5 days later at the same coordinates (0.5 mm anterior, 2 mm lateral (right), 3 mm deep to bregma). Animals were monitored daily and sacrificed when showing signs of morbidity. Data is presented as a Kaplan-Meier survival plot. Animals treated with KMMP9 or KGw survived significantly longer than those treated with PBS (P<0.01). No significant difference was found between KMMP9 and KGw (n=4; P=0.61, log-rank test).

Figure 10A:
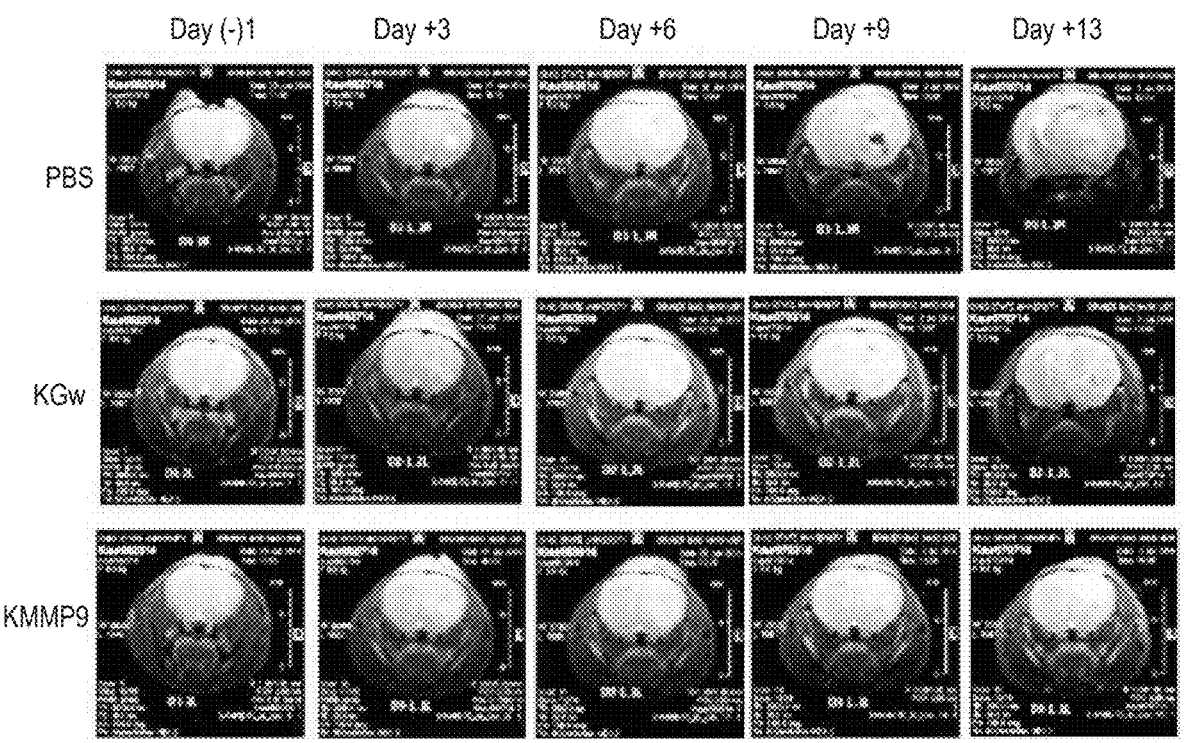
Figure 10B:
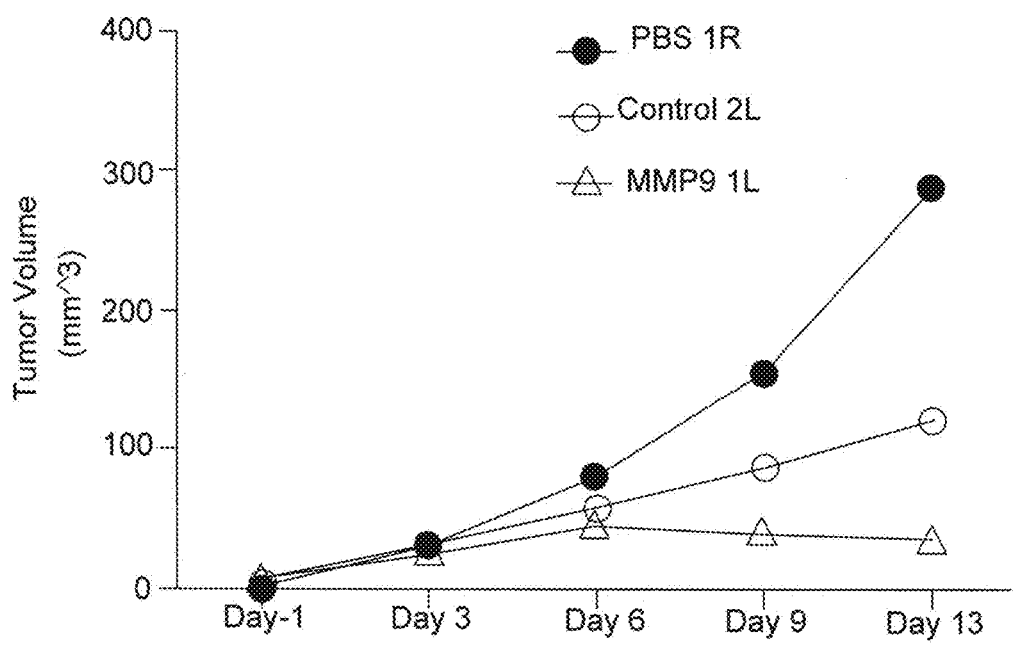

FIGS. 10A-10B depict T2-weighted brain MRI images of one animal per treatment of virus- or mock (PBS)-treated GBM30 animals. (A) Treatments were performed 10 days after GBM30 implantation and images were collected 1 day before treatment (Day −1) and on days 3, 6, 9 and 13 after treatment. (B) Calculated tumor volumes on the same days.

DETAILED DESCRIPTION OF THE INVENTION

The present invention provides a recombinant oHSV comprising a non-HSV ligand specific for a molecule (protein, lipid, or carbohydrate determinant) present on the surface of a cell (such as a cancer cell) and one or more copies of one or more microRNA target sequences inserted into one or more HSV gene loci, preferably one or more HSV gene(s) required for replication of HSV in normal (i.e., non-cancerous) cells. The invention further provides stocks and pharmaceutical compositions comprising the inventive oHSV and methods for killing tumor cells employing the inventive oHSV.

The non-HSV ligand of the inventive oHSV is incorporated into a glycoprotein exposed on the oHSV surface, such as gD or gC to facilitate targeting the desired cell with the ligand. For example, the ligand can be incorporated between residues 1 and 25 of gD. Preferred ligands for targeting GBM and other cancer cells include those targeting EGFR and EGFRvIII, CD133, CXCR4, carcinoembryonic antigen (CEA), C1C-3/annexin-2/M1V1P-2, human transferrin receptor and EpCAM, and the ligand can target such a receptor or cell-surface molecule, i.e., the ligand can be capable of specifically binding such receptor or cell-surface molecule. EGFR- and EGFRvIII-specific ligands, such as antibodies, scFvs (single chain antibodies) and VHHs (single domain antibodies), have been described in the literature (Kuan et al, *Int. J. Cancer,* 88, 962-69 (2000); Wickstrand et al., *Cancer Res.,* 55(14):3140-8 (1995); Omidfar et al., *Tumor Biology,* 25:296-305 (2004); see also Uchida et al. *Molecular Therapy,* 21:561-9 (2013); see also Braidwood et al., *Gene Ther.,* 15, 1579-92 (2008)).

The oHSV also or alternatively can be targeted by incorporating ligands to other cell-surface molecules or receptors that are not necessarily cancer-associated. For example, ligands can include binding domains from natural ligands (e.g., growth factors (such as EGF, which can target EGFR, NGF, which can target trkA, and the like)), peptide or non-peptide hormones, peptides selecting for binding a target molecule (e.g., designed ankyrin repeat proteins (DARPins)), etc. The inventive oHSV also can include a mutant form of gB and/or gH that facilitates vector entry though non-canonical receptors (and preferably also have such mutations in one or both of these genes within the oHSV genome).

A preferred microRNA target sequence for inclusion in the inventive vector (preferably as multiple copies thereof in tandem) is miR-124, which has particular application for neural applications (e.g., to protect non-cancerous neurons when employing the inventive oHSV for treating nervous-system tumors, such as GBM). Other microRNA target sequences can alternatively be employed for protecting other types of tissues, and it is within the ordinary skill in the art to select a suitable microRNA target sequence to protect a desired tissue or cell type. For example, miR-122 and miR-199 are expressed in normal liver cells but not primary liver cancer; thus one or a combination of miR-122 and/or miR-199 microRNA target sequences can be employed in an embodiment of the inventive oHSV for treatment of liver cancers. Similarly, target sequences for miR-128 and/or miR-137 microRNA can be employed in oHSV for protection of normal brain. An exemplary microRNA target sequence can be the reverse complement of the microRNA.

The microRNA target sequence(s) is/are preferably included in the 3' untranslated region ("UTR") of an HSV gene, to silence that gene in the presence of the microRNA. Preferably, multiple copies (such as two copies, three copies, four copies, five copies, six copies, or more) of the microRNA target sequence are inserted in tandem. Preferably, the multiple copies of the micro-RNA target sequence are separated by spacers of four or more nucleotides (more preferably eight or more nucleotides). Without wishing to be bound by theory, it is believed that greater spacing (e.g., larger than about 8 nucleotides) provides increased stability.

More preferably, to assist in protecting non-cancerous cells from the lytic effect of HSV infection, the multiple copies of the microRNA target sequence are inserted in the 3' UTR of an HSV gene that is essential for replication in non-cancerous cells, which are known to persons of ordinary skill. Preferably, the site is the 3' UTR of the microRNA-targeted gene in its normal (or native) locus within the HSV genome. A preferred oHSV of the present invention includes multiple copies of the microRNA target sequence inserted into the 3' UTR of the ICP4 gene, such as one or both copies of the ICP4 gene, in vectors which have both native copies of the ICP4 gene.

The genome of the inventive HSV vector additionally can comprise one or more exogenous expression cassettes (i.e., containing encoding-sequences in operable linkage with promoters, enhancers, and other suitable regulatory elements), such as encoding a reporter protein (such as green fluorescent protein), an oncolytic factor or agent that enhances tumor killing activity (such as tumor necrosis factor ("TNF") or TNF-related apoptosis-inducing ligand ("TRAIL"), or other therapeutically-important gene product (e.g., peptides, drug-activating enzymes, antibodies, therapeutic RNAs, and the like). A preferred exogenous expression cassette encodes a matrix metalloproteinase, such as matrix metalloproteinase 9 ("MMP9"), which degrades collagen type IV, a major component of the of the extracellular matrix (ECM) and basement membranes of glioblastomas (Mammato et al., *Am. J. Pathol.,* 183(4): 1293-1305 (2013), doi: 10.1016/j.ajpath.2013.06.026. Epub 2013 Aug. 5), thus enhancing infection of tumor cells by the inventive vector due to lateral spread and enhancing tumor-killing activity. Expression cassettes encoding other genes that enhance lateral spread of the inventive HSV are also preferred.

Other preferred exogenous expression cassettes encode proteins or polypeptides that induce patient immune responses against the cancer or tumor to which the inventive HSV is to be employed to treat. For example, such expression cassettes can include one or more nucleic acids encoding factors such as cytokines (e.g., IL-2 and IFN B), an antibody directed against cytotoxic T-lymphocyte-associated protein 4 ("CTLA-4") (Hodi et al., *N. Engl. J. Med.,* 363(8): 711-23 (2010)), an antibody directed against either the ligand of programmed cell death protein 1 ("PD1") or the receptor itself (Topalian et al., *N. Engl. J. Med.,* 366(26): 2443-54 (2012)), and epithelial cell adhesion molecule ("EpCAM") (Patriarca et al., *Cancer Treatment Rev.,* 38: 68-75 (2012)). As noted above, EpCAM also can serve as a targeting marker to be recognized by the inventive vector. Also, where the cancer to be treated is other than a CNS cancer, and more specifically other than glioma or glioblastoma, another transgene can encode granulocyte-macrophage colony-stimulating factor ("GM-CSF").

Other preferred expression cassettes encode proteins or polypeptides that catalyze the conversion of prodrugs to active agents. For example, such expression cassettes can encode enzymes such as cytosine deaminase, which can convert 5-fluorocytosine ("5-FC") into 5-fluorouracil ("5-FU") locally in tumors or cancerous cells infected with the inventive vector (see, e.g., Akimoto et al., *J. Ophthalmol.,* 86(5): 581-86 (2002)), so as to permit 5-FU to act locally within such cells or tumors while minimizing systemic exposure to 5-FU. Similarly, such an expression cassette can encode thymidine kinase (tk) (e.g., operably linked to a HSV immediate-early promoter or strong constitutive promoter), which can activate ganciclovir, or purine nucleoside phosphorylase (PNP), which can block or attenuate the activity of ribonucleotide reductase. In certain embodiments, the inventive vectors also can contain a functional native HSV tk gene.

Within the inventive vectors, the encoding sequences within the exogenous expression cassettes can be in operable linkage with any desired genetic regulatory sequence, such as constitutive promoters or inducible or tissue-specific promoters, many examples of which are known in the art. For example, a commonly-employed constitutive promoter is the human cytomegalovirus (hCMV) promoter, and other promoters also can be used, e.g., the CMV early enhancer/chicken beta actin (CAG) promoter, and HSV immediate early promoter (e.g., ICP4 promoter), and the like.

Also, in certain embodiments, the genome of the inventive vector contains a deletion of the internal repeat (joint) region comprising one copy each of the diploid genes ICP0, ICP34.5, LAT and ICP4 along with the promoter for the ICP47 gene. In other embodiments, instead of deleting the joint, the expression of genes in the joint region, particularly ICP0 and/or ICP47, can be silenced by deleting these genes or otherwise limited mutagenesis of them.

The inventive vector can be produced by standard methods known to persons of ordinary skill in the field of HSV virology. However, to facilitate manipulation of the HSV genome and production of the inventive vector, the invention also provides a nucleic acid encoding the inventive vector. A preferred nucleic acid is a bacterial artificial chromosome ("BAC") encoding the inventive vector, which facilitates manipulation of the HSV in a bacterial system.

It should be recognized that the inventive oHSV can be used to target and kill cancerous cells, whether in vivo or in vitro. A preferred application is to employ the inventive vector therapeutically, particularly in human patients and/or against human tumors/cells (which can be xenografts in various mammalian species). However, the method can also be employed in animals, such as companion animals (e.g., cats and dogs), or animals of agricultural importance (e.g., cattle, sheep, horses, and the like), or of zoological importance. Exemplary tumors/cancerous cells, the treatment of which the inventive vectors can be employed, involve cancers of the central nervous system, and in particular glioblastoma multiforme.

Generally, the inventive oHSV vector is most useful when enough of the virus can be delivered to a cell population to ensure that the cells are confronted with a suitable number of viruses. Thus, the present invention provides a stock, preferably a homogeneous stock, comprising the inventive oHSV vector. The preparation and analysis of HSV stocks is well known in the art. For example, a viral stock can be manufactured in roller bottles containing cells transduced with the oHSV vector. The viral stock can then be purified on a continuous nycodenze gradient, and aliquotted and stored until needed. Viral stocks vary considerably in titer, depending largely on viral genotype and the protocol and cell lines used to prepare them. Preferably, such a stock has a viral titer of at least about $10^5$ plaque-forming units (pfu), such as at least about $10^6$ pfu or even more preferably at least about $10^7$ pfu. In still more preferred embodiments, the titer can be at least about $10^8$ pfu, or at least about $10^9$ pfu, and high titer stocks of at least about $10^{10}$ pfu or at least about $10^{11}$ pfu are most preferred. Such titers can be established using cells that express a receptor to which the vector is targeted, for example.

The invention additionally provides a composition comprising the inventive oHSV vector and a carrier, preferably a physiologically-acceptable carrier. The carrier of the composition can be any suitable carrier for the vector. The carrier typically will be liquid, but also can be solid, or a combination of liquid and solid components. The carrier desirably is a pharmaceutically acceptable (e.g., a physiologically or pharmacologically acceptable) carrier (e.g., excipient or diluent). Pharmaceutically acceptable carriers are well known and are readily available. The choice of carrier will be determined, at least in part, by the particular vector and the particular method used to administer the composition. The composition can further comprise any other suitable components, especially for enhancing the stability of the composition and/or its end-use. Accordingly, there is a wide variety of suitable formulations of the composition of the invention. The following formulations and methods are merely exemplary and are in no way limiting.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of a sterile liquid excipient, for example, water, for injections, immediately prior to use. Extemporaneous injection solutions and suspensions can be prepared from sterile powders, granules, and tablets of the kind previously described.

In addition, the composition can comprise additional therapeutic or biologically-active agents. For example, therapeutic factors useful in the treatment of a particular indication can be present. Factors that control inflammation, such as ibuprofen or steroids, can be part of the composition to reduce swelling and inflammation associated with in vivo administration of the vector and physiological distress. Immune system suppressors can be administered with the composition method to reduce any immune response to the vector itself or associated with a disorder. Alternatively, immune enhancers can be included in the composition to upregulate the body's natural defenses against disease, particularly against the cancer or tumor against which the inventive vector is to be used. Antibiotics, i.e., microbicides and fungicides, can be present to reduce the risk of infection associated with gene transfer procedures and other disorders.

Example 1

Purpose: Glioblastoma multiforme (GBM) is an aggressive brain tumor without effective treatment. oHSV vectors have been designed for treatment of human GBM models in animals, but efficacy in patient trials has proved disappointing. We have sought to develop a new oHSV design that achieves highly selective tumor lysis without vector attenuation.

Experimental Design: We report an oHSV engineered to infect and replicate selectively in tumor cells by fully retargeting the infection through the EGFR and by blocking vector replication in normal neurons through the introduction of multiple copies of the sequence recognized by the neuronal-specific miR-124 into the 3'UTR of the essential ICP4 immediate early HSV gene. miR-124 was chosen because it is highly expressed in neurons but nearly undetectable in GBM. Vector was tested in xenogeneic brain-tumor treatment experiments for efficacy.

Results: High dose intracranial inoculation of nude mice with the miR-124-sensitive virus produced no evidence of pathogenesis or virus replication, consistent with blockage of viral replication in normal brain by miR-124 interaction with ICP4 mRNA. Treatment of an orthotopic model of primary human GBM in nude mice with EGFR-retargeted, miR124-sensitive HSV demonstrated long-term survival (>50%) comparable to treatment with the parental EGFR-retargeted virus, thus indicating that the miR-124 recognition elements did not lead to reduced efficacy.

Conclusions: We conclude that the specificity of unattenuated oHSV can be maximized by combining tumor targeting of vector infection with elimination of off-target vector replication through cellular microRNAs that are absent in tumors but highly expressed in normal tissue.

Introduction

GBM is one of the most malignant forms of cancer for which effective treatment remains elusive. Standard medical practice such as surgery and radio- and chemotherapy have shown limited long-term clinical benefit. Oncolytic vectors, including those derived from herpes simplex virus type-1 (oHSV-1), are under development in a number of laboratories as a potential alternative therapeutic strategy (1). oHSV vectors have shown promise for the treatment of animal models of primary GBM, but aside from providing a good safety profile, results from early phase clinical trials have not demonstrated effective tumor killing or consistent improvements in patient survival (2) (3).

The most common method to achieve HSV attenuation has been to functionally delete non-essential genes that circumvent host innate immune responses to infection, provide nucleotide pools for replication in non-dividing cells such as neurons, and prevent cellular apoptosis (2). Virus replication in cancer cells is facilitated by the loss of certain innate immune responses (4), as well as by rapid cell division and inactive apoptotic pathways (2). However, these properties are not uniformly sufficient for vigorous replication of current oHSVs in tumors.

As a first step to improve vector efficacy we previously developed methods for complete retargeting of HSV in order to redirect infection from the canonical HSV entry receptors to highly expressed tumor cell-surface receptors (e.g. EGFR and EGFRvIII) (5). Retargeted oHSV showed robust oncolytic activity and high specificity for human GBM cells, resulting in a high level of human tumor destruction in an orthotopic mouse model. Moreover this treatment vector produced long-term survival of the majority of treated animals without vector-associated toxicity. However, most highly expressed tumor-associated cell surface markers are shared to some degree with normal cell types and thus we sought to increase the safety of a tumor-targeted, unattenuated vector using an independent mechanism to block virus replication in normal brain without reducing replication in the tumor.

Recent studies have taken advantage of differences in the microRNA (miRNA) expression profiles between normal and cancer cells as an alternative approach to tumor targeting (6). At least 30 miRNAs have been identified that are differentially expressed in glioblastoma, neurons and neural precursor cells (NPCs) (7) (8), suggesting that these differences can be used to limit virus replication in normal brain cells while permitting unimpeded replication in tumor cells. Here we demonstrate that the incorporation of miR-124 recognition elements into the essential ICP4 gene of essentially wild type virus prevented HSV replication in normal brain tissue where miR-124 is highly expressed. Furthermore, we show that the miR-124 response elements did not reduce the oncolytic activity of an EGFR-retargeted vector. Importantly, since the tumor phenotype depends on the continued absence of miR-124, potential up-regulation of miR-124 as a cellular escape mechanism from lytic viral replication will limit the uncontrolled proliferative capacity of the cell and thereby not compromise vector effectiveness. Vector production is carried out in cells lacking miR-124 and thus there is no selective pressure to produce miR-124-resistant virus mutants during stock preparation. Together, these features provide for vector safety and tumor selectivity and suggest a general strategy for oncolytic vector design suitable for a broad range of tumor types.

Results

Validation of a miR-124 response element. Among multiple miRNAs that are expressed at higher levels in neurons than in GBM cells, miR-124 is the most abundant with minimal expression in GBM (6). We designed a miR-124 response element (T124) consisting of 4 tandem copies of the reverse complement of mature miR-124 separated by different 8 nucleotide (nt) spacers. To assess the functionality of this sequence, we inserted it into the 3'UTR of a firefly luciferase (fLuc) expression plasmid and performed co-transfection experiments with a specific (pre-miR-124) or non-specific (pre-miR-21) precursor miRNA on U2OS osteosarcoma cells that reportedly express little or no miR-124 (9); a *Renilla* luciferase (rLuc) expression plasmid was included for normalization. The results (pfLuc-T124, FIG. 1) showed severely reduced fLuc activity at 24 h in cells co-transfected with pre-miR-124 compared to mock co-transfected cells or cells co-transfected with pre-miR-21. In contrast, little difference in fLuc expression was observed between cells transfected with a control fLuc plasmid containing 4 copies of the miR-21 sequence in reverse (pfLuc-Ctrl, mock) and co-transfections of pfLuc-Ctrl with either pre-miR-21 or pre-miR-124 (FIG. 1). These results demonstrated the functionality of the T124 element as an efficient and specific target for miR-124-mediated restriction of gene expression.

Figure 2A:
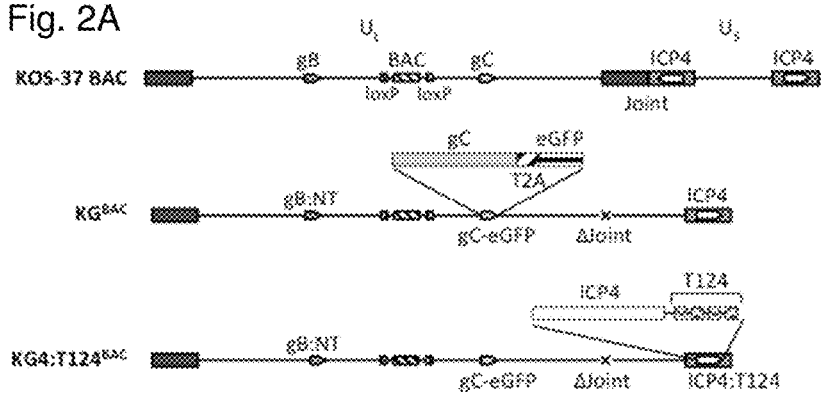
Figure 2B:
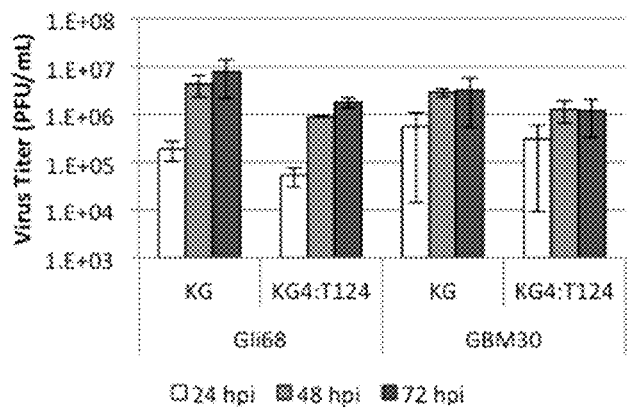

Replication sensitivity of T124-modified HSV to miR-124 expression. We used double Red recombination in *E. coli* 0) to introduce a series of modifications into KOS-37 BAC, a full-length genomic clone of the KOS strain of HSV-1 on a bacterial artificial chromosome (BAC) (11). The product, $KG^{BAC}$ (FIG. 2A), is deleted for the internal repeat (joint) region containing one copy each of the diploid genes ICP0, ICP34.5, LAT and ICP4 along with the promoter for the ICP47 gene. This deletion facilitates manipulation of the remaining copies of the 4 deleted genes, provides abundant space for the potential incorporation of transgenes that enhance the oncolytic activity of the virus, and increases tumor specificity by reducing expression of the neurovirulence factor ICP34.5 (12); elimination of ICP47 expression benefits immune recognition of infected cancer cells by virus-specific T cells (4). $KG^{BAC}$ also contains the GFP open reading frame (ORF) fused to the glycoprotein C (gC) ORF via a 2A peptide sequence (13) (14) to allow monitoring of late (post-replication) viral gene expression. Lastly, $KG^{BAC}$ contains a pair of mutations in the gB gene shown by us to enhance HSV entry through non-canonical receptors (15) (16). We recombined the T124 sequence into the 3'UTR of the remaining ICP4 gene of $KG^{BAC}$ to generate KG4: $T124^{BAC}$ (FIG. 2A). Both BAC constructs were converted to virus particles with simultaneous removal of the BAC sequences located between loxP sites by transfection of U2OS-Cre cells. Following plaque purification, KG and KG4:T124 virus stocks were prepared and titered on U2OS cells.

Figure 2C:
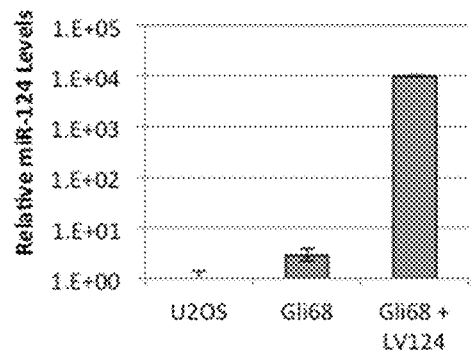
Figure 2D:
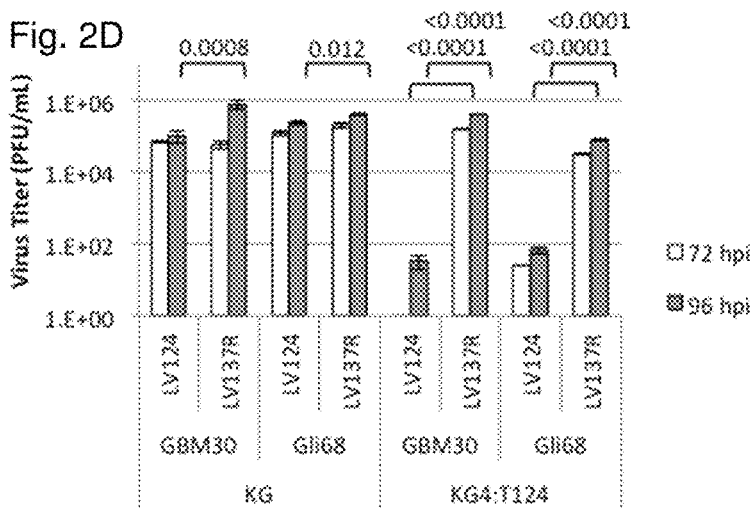

We first determined whether inclusion of the 4 tandem miR-124 target sites in the 3'UTR of ICP4 affected virus replication in human GBM cells in culture. The results (FIG. 2B) showed that KG4:T124 replicated with similar kinetics as KG in spheroids of two primary glioblastoma lines, Gli68 and GBM30, and the yields of the 2 viruses were not substantially different at each time point. We then determined whether replication and virus yield were sensitive to transduction of these lines with a human miR-124 expressing lentivirus (LV124). FIG. 2C shows the relative levels of miR-124 in U2OS, Gli68, and Gli68-LV124 cells measured by real-time qPCR on reverse transcribed small RNAs and standardized to endogenous RNU43 levels. KG grew equally well and to similar titers on Gli68-LV124 and Gli68 cells transduced with a lentiviral construct expressing the reverse complement of human miR-137 (LV137R) (FIG. 2D). In contrast, KG4: T124 grew poorly on the former compared to the latter, and similar results were obtained with LV124-versus LV137R-transduced GBM30 cells (FIG. 2D). In combination, these observations strongly indicated that (i) the T124 element in the ICP4 gene was effective as a means to limit HSV replication in a miR-124-dependent manner, and (ii) the levels of endogenous miR-124 in the 2 GBM lines were low enough to minimize this effect. In addition, the qRT-PCR data confirmed the suitability of U2OS cells for unimpaired growth and titration of KG4:T124 compared to KG.

KG4:T124 does not replicate in mouse brain or cause disease. Having shown that exogenous miR-124 expression in primary glioma cells in culture is highly effective in preventing KG4:T124 vector growth, we next tested whether the endogenous levels of miR-124 in mouse brain were sufficient to prevent vector replication and the typical neuropathogenesis associated with wild-type virus; we note that mature human and mouse miR-124 are identical in sequence (17). We used nude mice for these experiments to limit the effect of the host anti-viral response and thereby facilitate the identification of direct effects of the T124 insertion in the virus. BALB/$c^{nu/nu}$ mice were chosen because these animals are highly sensitive to HSV replication and pathogenesis (18) (19) (20) and have been used previously for tumor treatment efficacy experiments with human tumor cells (21) (12, 22) (5). We compared the KG control vector and the miR-124-sensitive test vector KG4: T124 for their ability both to replicate in nude mouse brain and cause a lethal infection following intracranial inoculation of equal genome copy (gc) numbers (4.8×10$^9$ gc) into the right hemisphere. The results showed that injection of the control vector resulted in rapid animal death within 5 days (FIG. 3A, C) with a two-fold increase in total gc number present within the infected brains (FIG. 3B). In contrast, there was no observable change in the health of the KG4:T124 injected mice over the 33-day observation period, as exemplified by their normal weight gain until sacrifice (FIG. 3A), and the viral gc content declined steadily over this time period to approximately 0.4% of input (FIG. 3B). The difference in survival between the animals inoculated with control or test vector (FIG. 3C) was highly significant (P=0.0058, log-rank test), indicating that 4 copies of the miR-124 recognition sequence inserted into the 3'UTR of the ICP4 gene were capable of blocking lethal vector replication in the brains of highly HSV-sensitive nude mice. Thus these sequences alone were sufficient to prevent vector toxicity in the brain.

To confirm the suggestion from these results that loss or mutational inactivation of the miR-124 target sites during virus stock preparation was rare at best, DNA was isolated from the KG4:T124 viral stock and subjected to PCR through the T124 insertion site in the ICP4 3'UTR. Analysis of the products by gel electrophoresis and DNA sequencing showed no abnormal PCR product sizes or evidence of nucleotide variability (data not shown). Likewise, PCR and sequence analyses of total brain DNA isolated at 3 h or 21 d post intracranial inoculation of normal BALB/c mice with KG4:T124 virus ($1.5 \times 10^{10}$ gc) showed no abnormalities through the T124 region (data not shown). These results allayed concerns about potential selection of miR-124-insensitive variants during KG4:T124 virus growth or in vivo.

The miR-124 response elements do not impair EGFR-targeted oncolytic HSV activity. We next sought to ascertain whether the protective miR-124 recognition elements adversely affected the viral tumor-killing activity in a nude-mouse model of human GBM. Since KG was highly toxic when inoculated into the brains of these animals (FIG. 3C), the use of this virus as a treatment control in survival experiments of tumor-bearing mice could result in animal death due to the virus rather than the tumor and thus was not attractive. Instead, we introduced the 4 copies of the miR-124 binding site into a fully EGFR-retargeted derivative of KG based on our published observations that fully EGFR-retargeted wild-type HSV-1 KOS is non-toxic for nude mouse brain but is effective in the treatment of orthotopic human GBM in nude mice (5). Thus comparison of EGFR-retargeted versions of KG and KG4:T124, referred to as KGE and KGE-4: T124, respectively, should identify any limiting effects of the miR-124 sites on viral oncolytic activity. We used patient-derived, sphere-forming GBM30 cells to establish aggressive intracranial tumors in nude mice (5). Animals were observed daily and euthanized when showing signs of morbidity. Similar to our published results, mice injected with PBS 5 d after tumor-cell inoculation at the same stereotactic coordinates died within weeks of tumor-cell implantation (median 21.5 d; FIG. 4A, B). In contrast, tumor treatments using either the EGFR-retargeted control virus, KGE, or the T124-containing retargeted vector, KGE-4:T124, protected half of the animals for the duration of the experiment (90 d) and the median survival times for these two groups were comparable (79.5 and 85.5 d, respectively; P=0.83, log-rank test). These results indicated that the miR-124 sites in the ICP4 gene of KGE-4: T124 did not impair GBM30 tumor treatment efficacy.

Discussion

Our goal was to engineer an oncolytic HSV vector that expresses the full complement of viral functions but can only infect cells expressing a GBM-associated receptor and replicate with high efficiency only in the tumor and not in normal brain cells. Tumor-selective infection and lytic virus growth relied on a combination of complete viral entry retargeting (5) and cellular miRNA-mediated restriction of virus replication in normal brain tissue. This combination of transductional and post-transcriptional tumor targeting promises to provide a very safe and effective oHSV since lytic infection requires two separate characteristics of the target cell that are important for maintenance of the tumor phenotype, the targeted receptor and a tumor-specific miRNA expression profile. This general strategy is broadly applicable using targeting and miRNA-response elements tailored to different cancers; its application can be optimized for personalized therapy by taking into account potential differences in specific antigen and miRNA expression between individual tumors of the same type.

In GBM, altered gene expression includes substantial down-regulation of multiple miRNAs compared to normal brain tissue (23-25), presenting several possible miRNAs that may be used to preferentially attenuate engineered virus replication in normal brain. Because miR-124 is recognized as a potent inducer of neuronal differentiation (26) and is among the most highly down-regulated miRNAs in GBM (6), we focused on this miRNA as a means to block oHSV replication in normal brain tissue. Repeat recognition sites for miR-124 (T124) were introduced into the 3'UTR of the viral ICP4 gene whose product is absolutely required for launching the HSV lytic cycle. We found that in glioma cells, the T124+ virus could replicate essentially as robustly as the control virus lacking T124 whereas lentiviral expression of miR-124 selectively blocked its replication. Furthermore, the T124 element was sufficient to completely protect nude mice from very high intracranial vector dosing ($4.8 \times 10^9$ particles) while the control vector killed all animals within five days. Determination of total viral genome copy numbers in the brains of these animals showed no evidence of T124+ vector replication but rather a gradual decrease in viral genome content over time. The T124 sequence was stable as assessed by size and sequence analysis of the ICP4 3'UTR amplified on purified DNA from virus stocks and infected animals, consistent with the lack of overt neuro-pathogenesis in tumor-free animals or long-term survivors from our tumor treatment experiment. Finally, we used a retargeted virus that fails to infect mouse cells to demonstrate that the T124 element did not reduce the oncolytic efficacy of this virus in a human GBM model in nude mice.

The combination of virus targeting to tumor receptors and miRNA-mediated blocking of virus replication in normal cells enhances the target specificity of the lytic virus by blocking productive infection of normal cells that may share the targeted receptor with the tumor (e.g., EGFR). While our results show that the insertion of four copies of the target sequence for miR-124 into the 3'UTR of the ICP4 gene completely blocks very high dose viral neuro-pathogenesis in nude mice, not all brain cells express miR-124. For example, neuronal precursor cells (NPCs) located in the hippocampus and sub-ventricular zone (SVZ) are not expected to be protected by the miR-124 target sequences since these cells have an miRNA expression profile that is similar to that of GBM cells, including minimal expression of miR-124 (27). However, several miRNAs are expressed at up to 100-fold higher levels in NPCs than in gliomas (27) (28) (29) (30), suggesting the possibility of using target sites for additional miRNAs engineered into the same or other essential genes of the same virus to block replication in a wider range of brain cells without compromising tumor specific virus replication.

Although our study suggests that the combination of virus targeting to a tumor antigen and miRNA-restricted replication in normal tissue is an attractive strategy for effective and highly specific tumor virotherapy, it is likely that individual tumors will differ in their response to the treatment due to variability in tumor antigen levels and perhaps miRNA content. For example, there are significant differences between tumors classified as GBM, and even within the molecularly defined GBM subtypes, heterogeneity in gene expression profiles remains (31). Thus a single retargeted virus will not be effective against all GBM or all GBM of the same subtype. In addition, it may be anticipated that resistant cell populations can emerge in largely oHSV-sensitive tumors as a consequence of pre-existing or treatment-induced cell-to-cell variability within the tumor. Developments over the past several years suggest that the small population of self-renewing, chemo- and radio-resistant cancer stem cells (CSCs) identified in many different tumor types are the most relevant targets for therapy (32). Although comparison of individual CSCs from a given tumor is problematic, it is likely that their variability within a tumor is limited relative to that of the complete tumor-cell population. Reports in the literature describe different glioma stem cell (GSC) markers (33) and retargeted oncolytic viruses can be used to distinguish the significance of each of these for human GBM establishment and maintenance in nude mice. We anticipate that tumors showing partial responses to individual retargeted vectors may be more effectively treated with combinations of vectors retargeted to different GSC candidate markers. Since each of these vectors may also target certain normal cells, similar to our EGFR-retargeted viruses, miRNA-mediated blockage of virus replication in these normal cells will be of increasing importance. In addition, it may be possible to gain further specificity using cell type- or developmental stage-specific promoters to control the expression of key viral replication functions, as pioneered in the oHSV field by Kambara and colleagues (34). While these features may provide highly active and specific oncolytic vector cocktails, it is noteworthy that vectors such as KGE-4:T124 have ample space to accommodate transgenes that may enhance therapeutic efficacy, such as genes encoding immune modulators, inhibitors of tumor cell migration, or proteolytic enzymes that degrade the tumor extracellular matrix and thereby facilitate intratumoral virus spread.

In summary, the KGE-4:T124 vector described in this Example represents a novel type of oHSV that contains the complete complement of virus replicative functions, but derives tumor specificity from a combination of viral envelope retargeting to tumor-associated receptors and replication sensitivity to miRNAs that are expressed in normal tissue but not in the tumor. This combination of control systems can be applied to other tumor types but has not been previously described in oncolytic vectors. Key advantages of our strategy are (i) that the vector does not contain any defective genes, allowing maximal virus replication in tumors to provide optimal oncolytic virotherapy, and (ii) that vector replication requires both the expression of important tumor-associated cell-surface markers and a tumor-specific profile of miRNA expression that differs substantially from that of normal tissue. The most compelling argument for our strategy is that miRNAs chosen to control vector replication in normal brain cannot be up-regulated in glioblastoma without compromising the tumor phenotype (7, 25, 35); loss of the targeted receptor, such as the tumor-specific EGFRvIII variant recognized by our vector, may have a similar effect. Thus, while in most cancer therapies the tumor develops the ability to escape treatment, this outcome is less likely with tumor antigen-targeted, miRNA-regulated viruses. Together, these arguments support the expectation that our approach will provide highly selective, safe and effective oncolytic HSV vector systems for the treatment of GBM and other cancers.

Materials and Methods

Cell culture. U2OS, HEK293T and HEK293AD cells were from ATCC (Manassas, VA) and were grown in a 5% $CO_2$ incubator at 37° C. in ATCC-recommended medium supplemented with 5-10% (v/v) fetal bovine serum (FBS; Sigma, St. Louis, MO). A U2OS cell line stably expressing Cre recombinase (U20S-Cre) was generated by retroviral transduction (Y. M. and J. C. G., unpublished results). GBM30 and Gli68 patient-derived primary glioma spheroid lines, generously provided by E. A. Chiocca (Harvard Medical School, MA), were grown in Neurobasal medium (Gibco/Invitrogen/Life Technologies, Carlsbad, CA) plus 2% (v/v) B27 w/o vitamin A, 2 mg/mL amphotericin B (Lonza, Walkersville, MD), 100 µg/mL gentamycin (Lonza), 2 mM L-glutamine (Cellgro, Manassas, VA), plus 10 ng/mL recombinant human epidermal growth factor (rhEGF) and 10 ng/mL recombinant human basic fibroblast growth factor (bFGF) (both from Shenandoah Biotechnology, Warwick, PA).

Plasmids. pfLuc-T124 contains four tandem repeats of the reverse complement of the hsa-miR-124 sequence separated by 8 nt, while pfLuc-Ctrl contains four tandem repeats of the hsa-miR-21 reverse sequence separated by 8 nt. Both plasmids were constructed by insertion of annealed complementary oligonucleotides into the 3'UTR of the luciferase gene in pMIR-REPORT™ (miRNA Expression Reporter Vector System; Ambion, Austin, TX). Oligonucleotides were T124-F, T124-R, TconF and TconR (Table 1). Annealed oligonucleotides were digested with SpeI and SacI, and ligated to SpeI-SacI-digested pMIR-REPORT™.

HSV genome engineering. KOS-37 BAC (11), containing the complete strain KOS HSV-1 genome on a bacterial artificial genome (BAC), was kindly provided by David Leib (Dartmouth Medical School, NH). The HSV unique short (Us) region in this BAC is in the reverse orientation relative to the published sequence (positions 132,275-145, 608) of HSV-1 KOS (36) (GenBank Accession number JQ673480). Modifications detailed further below were introduced by double Red recombination, essentially as described by Tischer et al. (10). Plasmids pEPkan-S and pBAD-I-sceI (10) were generously provided by Nikolaus Osterrieder (Free University of Berlin, Germany). Changes were verified by PCR analysis, FIGE analysis of restriction enzyme digests, and local DNA sequencing.

Vectors used in this study were sequentially derived as follows. $KG^{BAC}$ was derived from KOS-37 BAC by deletion of the complete HSV internal repeat region or "joint" (IRL, IRs), fusion of the green fluorescent protein (GFP) open reading frame (ORF) to the glycoprotein C (gC) ORF via the *Thosea asigna* virus 2A (T2A) translation termination/reinitiation sequence (13) (37), and introduction of two missense mutations in the gB coding sequence (gB:N/T; (15). KG4: $T124^{BAC}$ was created from $KG^{BAC}$ by insertion of the T124 element from pfLuc-T124 into the 3'UTR of the ICP4 gene. The retargeted vector $KGE^{BAC}$ was derived from $KG^{BAC}$ by replacement of the amino-terminal region of the gD gene with the corresponding region of gD-scEGFR containing the sequence for a human EGFR-specific single chain antibody between gD positions 1 and 25 and a missense mutation at codon 38 (D. KGE-4:T124$^{BAC}$ combines the modifications from KG4:T124$^{BAC}$ and KGE$^{BAC}$.

Virus growth and purification. BAC DNAs were converted to infectious virus by transfection of U2OS-Cre cells using Lipofectamine™ LTX Reagent (Invitrogen); Cre recombinase expressed in these cells allowed the removal of the virus growth-inhibitory BAC elements and adjacent lacZ gene located in KOS-37 BAC and derivatives between loxP recombination signals (1.1_). Single plaques were isolated by limiting dilution and tested for elimination of the lacZ gene by X-gal staining (3). Colorless plaques were subjected to two additional rounds of limiting dilution and accurate removal of the BAC/lacZ region was confirmed by local DNA sequencing of purified virion DNA. Biological titers of virus stocks (PFU/mL) were established on U2OS cells; physical titers in genome copies (gc)/mL were determined by quantitative real-time PCR (qPCR) for the viral gD gene, as described below.

Luciferase assay. HEK293AD cells were transfected with the *renilla* luciferase expression plasmid prLuc together with combinations of different firefly luciferase expression plasmids and pre-miR™ miRNA Precursors (Ambion) using Lipofectamine 2000 (Invitrogen). The next day, cells were lysed and the firefly-to-renilla luciferase expression ratios were determined using a Berthold LB-953 AutoLumat luminometer (Berthold Technologies USA, Oak Ridge, TN).

Lentiviral expression of miRNAs. Genomic DNA from U-87 human glioblastoma cells was used as template for PCR amplification of the human pri-miR-124 sequence from the hsa-miR-124-3 gene using High Fidelity Accuprime GC-rich DNA Polymerase (Invitrogen) and the miR-124 primer pair listed in Table 1. The 320-bp product was digested with BamHI and NheI, cloned between the corresponding sites in the intron of miRNASelect pEP-miR vector (Cell Biolabs, San Diego, CA), and sequence confirmed. The promoter-intron-pri-miR-124 region was subsequently transferred into pCDH-CMV-MCS-EF1-Puro (System Biosciences, Mountain View, CA) by replacement of the resident EF1 promoter to generate lentiviral expression plasmid pCDH-miR-124. The same procedures were used to construct the control lentiviral plasmid (pCDH-miR-137R) containing the pri-miR-137 sequence in the reverse orientation; the PCR primers used for pri-miR-137 cloning are listed in Table 1. Lentiviruses LV124 and LV137R were produced by co-transfection of pCDH-miR-124 or pCDH-miR-137R, respectively, with packaging plasmids pLP1, pLP2, pLP-VSVG (Invitrogen) into HEK293T cells. Supernatants were harvested 72 h later, passed through a 0.45 μm filter (Millipore, Billerica, MA), and concentrated by centrifugation for 16 h at 4° C. and 6,800×g. Pellets were resuspended in DMEM and titered as puromycin-resistant colony-forming units (cfu) per mL on HEK293T cells.

2×10$^5$ triturated Gli68 or GBM30 cells were infected in suspension with either LV124 or LV137R at 5 cfu/cell in the presence of 8 μg/mL polybrene for 90 min and plated. The cells were fed the following day with fresh media containing 30 μg/mL puromycin and super-infected 72 h later with either KG or KG4: T124 virus at an MOI of 0.01 pfu/cell. At 72 and 96 h post HSV infection, infectious virus particles were collected from cells and supernatants and titered on U2OS cells. RNA was isolated from parallel cultures of LV124-infected Gli68 cells after 72 h of puromycin selection for determination of miR-124 levels by qRT-PCR, as described below.

RNA isolation and reverse transcription (RT)-qPCR. Total RNA was extracted from U2OS, Gli68, and LV124-infected Gli68 cells using TRIzol Reagent (Invitrogen) according to the manufacturer's instructions. RNA samples were treated with DNase I (Invitrogen), quantified using a NanoDrop 2000c spectrophotometer (Thermo-Fisher, Pittsburgh, PA) and visualized on a MOPS-formaldehyde gel for quality assurance. Mature hsa-miR-124 levels were determined relative to RNU43 according to the TaqMan Small RNA Assays Protocol (Applied Biosystems/Life Technologies, Carlsbad, CA). TaqMan primers and probes were from Applied Biosystems. All TaqMan PCR reactions were performed in triplicate.

Animals. 3-4 week-old BALB/c athymic nu/nu mice were purchased from Charles River Laboratory (Wilmington, MA) and housed in a BSL2 facility. All animal procedures were performed in accordance with the requirements and recommendations in the Guide for the Care and the Use of Laboratory Animals (Institute for Laboratory Animal Research, 1985) as approved by the University of Pittsburgh Institutional Animal Care and Use Committee (IACUC).

Intracranial toxicity. Intracranial virus inoculations were performed a described (5). Mice received 4.8×10$^9$ gc of KG or KG4:T124 virus (n=4/group). The animals were monitored daily for signs of morbidity and were weighed every other day. All mice of the KG group died by day 5 and one mouse of the other group was sacrificed the same day. Remaining animals of the KG4:T124 group were sacrificed on days 14, 21 and 33. Whole brains were collected from euthanized mice for total DNA extraction and qPCR for viral genomes, as described below.

qPCR for viral genomes. DNA was extracted from mouse brains or virus stocks using the DNeasy Blood & Tissue kit (Qiagen, Valencia, CA) according to the manufacturer's procedure. A standard curve for qPCR was generated on DNA from a pENTR1A (Invitrogen) plasmid containing the complete HSV-1 (strain KOS) gD coding sequence (pE-gD18) using the protocol described in the Applied Biosystems StepOne™ and StepOnePlus™ Real-Time PCR Systems manual. Primers and probe sequences are listed in Table 1.

TABLE 1

| Target | Sequence |
|---|---|
| | Forward |
| T124 (pfLuc-T124) | 5'-P-ctagtGGCATTCACCGCGTGCCTT AtagtaccagGGCATTCACCGCGTGCCTTA aggatcctGGCATTCACCGCGTGCCTTAatg actgcGGCATTCACCGCGTGCCTTAgagct-3' SEQ ID NO: 1 |
| Tcon (pfLuc-Ctrl) | 5'-P-ctagtGCGGCCGCgtctcgggaccgcactc gttATCGAATAGTCTGACTACAACTtagtac cagATCGAATAGTCTGACTACAACTaggat cctATCGAATAGTCTGACTACAACTatgact gcATCGAATAGTCTGACTACAACTctcgacct 3' SEQ ID NO: 2 |
| Pri-miR124 (LV124) | 5'-TCGAGGATCCTGTCAGTGCGCACGCACAC-3' SEQ ID NO: 3 |
| Pri-miR137R (LV137R) | 5'-TCGAGGATCCAAACACCCGAGGAAATGAAAAG-3' SEQ ID NO: 4 |
| gD (qPCR) | 5'-CCCCGCTGGAACTACTATGACA-3' SEQ ID NO: 5 |

TABLE 1-continued

| | Reverse |
|---|---|
| T124 (pfLuc-T124) | 5'-P-cTAAGGCACGCGGTGAATGCCg<br>cagtcatTAAGGCACGCGGTGAATGC<br>CaggatcctTAAGGCACGCGGTGAAT<br>GCCctggtactaTAAGGCACGCGGTGAATGCCa-3'<br>SEQ ID NO: 6 |
| Tcon (pfLuc-Ctrl) | 5'-P-cgagAGTTGTAGTCAGACTATTC<br>GATgcagtcatAGTTGTAGTCAGACT<br>ATTCGATaggatcctAGTTGTAGTCAG<br>ACTATTCGATctggtactaAGTTGTAG<br>TCAGACTATTCGATaacgagtgcggtccc<br>gagacGCGGCCGCa-3'<br>SEQ ID NO: 7 |
| Pri-miR124 (LV124) | 5'-TGCAGCTAGCCAGACCCCTCCCCTCGC-3'<br>SEQ ID NO: 8 |
| Pri-miR137R (LV137R) | 5'-TCGAGCTAGCGCTCAGCGAGCAGCAAGAGTTC-3'<br>SEQ ID NO: 9 |
| gD (qPCR) | 5'-GCATCAGGAACCCCAGGTT-3'<br>SEQ ID NO: 10 |

| | Probe |
|---|---|
| | 5'-FAM-TTCAGCGCCGTCAGCGAGGA-TAMRA-3'<br>SEQ ID NO: 11 |

Tumor model and treatment. Intracranial implantation of human GBM30 cells into nude mice was performed as described (D. At 5 d, viruses ($1.8 \times 10^8$ gc of KGE or KGE-4:T124, n=8/group) or PBS (n=2) were inoculated at the same coordinates, as also described (5). Animal health and well-being were monitored as described above under "Intracranial toxicity." Animals were euthanized when showing signs of morbidity.

Statistical analysis. Unpaired t test with Welch's correction was performed using GraphPad Prism version 6.01 for Windows (GraphPad Software, La Jolla, CA; www.graphpad.com). Animal survival data were charted as Kaplan-Meier plots and compared by Mantel-Cox log-rank test using the same software.

References for Example 1

1. Parker J N, Bauer D F, Cody J J, Markert J M. Oncolytic viral therapy of malignant glioma. Neurotherapeutics. 2009; 6:558-69.
2. Grandi P, Peruzzi P, Reinhart B, Cohen J B, Chiocca E A, Glorioso J C. Design and application of oncolytic HSV vectors for glioblastoma therapy. Expert Rev Neurother. 2009; 9:505-17.
3. Markert J M, Medlock M D, Rabkin S D, Gillespie G Y, Todo T, Hunter W D, et al. Conditionally replicating herpes simplex virus mutant, G207 for the treatment of malignant glioma: results of a phase I trial. Gene therapy. 2000; 7:867-74.
4. Todo T. Oncolytic virus therapy using genetically engineered herpes simplex viruses. Frontiers in bioscience: a journal and virtual library. 2008; 13:2060-4.
5. Uchida H, Marzulli M, Nakano K, Goins W F, Chan J, Hong C S, et al. Effective treatment of an orthotopic xenograft model of human glioblastoma using an EGFR-retargeted oncolytic herpes simplex virus. Molecular therapy: the journal of the American Society of Gene Therapy. 2013; 21:561-9.
6. Gaur A, Jewell D A, Liang Y, Ridzon D, Moore J H, Chen C, et al. Characterization of microRNA expression levels and their biological correlates in human cancer cell lines. Cancer research. 2007; 67:2456-68.
7. Karsy M, Arslan E, Moy F. Current Progress on Understanding MicroRNAs in Glioblastoma Multiforme. Genes & cancer. 2012; 3:3-15.
8. Riddick G, Fine H A. Integration and analysis of genome-scale data from gliomas. Nature reviews Neurology. 2011; 7:439-50.
9. Kumar M S, Lu J, Mercer K L, Golub T R, Jacks T. Impaired microRNA processing enhances cellular transformation and tumorigenesis. Nature genetics. 2007; 39:673-7.
10. Tischer B K, von Einem J, Kaufer B, Osterrieder N. Two-step red-mediated recombination for versatile high-efficiency markerless DNA manipulation in *Escherichia coli*. Biotechniques. 2006; 40:191-7.
11. Gierasch W W, Zimmerman D L, Ward S L, Vanheyningen T K, Romine J D, Leib D A. Construction and characterization of bacterial artificial chromosomes containing HSV-1 strains 17 and KOS. J Virol Methods. 2006; 135:197-206.
12. Bennett J J, Delman K A, Burt B M, Mariotti A, Malhotra S, Zager J, et al. Comparison of safety, delivery, and efficacy of two oncolytic herpes viruses (G207 and NV1020) for peritoneal cancer. Cancer gene therapy. 2002; 9:935-45.
13. Szymczak A L, Vignali D A. Development of 2A peptide-based strategies in the design of multicistronic vectors. Expert Opin Biol Ther. 2005; 5:627-38.
14. Doronina V A, Wu C, de Felipe P, Sachs M S, Ryan M D, Brown J D. Site-specific release of nascent chains from ribosomes at a sense codon. Mol Cell Biol. 2008; 28:4227-39.
15. Uchida H, Chan J, Goins W F, Grandi P, Kumagai I, Cohen J B, et al. A double mutation in glycoprotein gB compensates for ineffective gD-dependent initiation of herpes simplex virus type 1 infection. Journal of virology. 2010; 84:12200-9.
16. Uchida H, Chan J, Shrivastava I, Reinhart B, Grandi P, Glorioso J C, et al. Novel Mutations in gB and gH Circumvent the Requirement for Known gD Receptors in Herpes Simplex Virus 1 Entry and Cell-to-Cell Spread. Journal of virology. 2013; 87:1430-42.
17. Cao X, Pfaff S L, Gage F H. A functional study of miR-124 in the developing neural tube. Genes & development. 2007; 21:531-6.
18. Fujioka N, Akazawa R, Ohashi K, Fujii M, Ikeda M, Kurimoto M. Interleukin-18 protects mice against acute herpes simplex virus type 1 infection. Journal of virology. 1999; 73:2401-9.
19. Manickan E, Rouse R J, Yu Z, Wire W S, Rouse B T. Genetic immunization against herpes simplex virus. Protection is mediated by CD4+T lymphocytes. Journal of immunology. 1995; 155:259-65.
20. Sethi K K, Omata Y, Schneweis K E. Protection of mice from fatal herpes simplex virus type 1 infection by adoptive transfer of cloned virus-specific and H-2-restricted cytotoxic T lymphocytes. The Journal of general virology. 1983; 64 (Pt 2):443-7.
21. Currier M A, Gillespie R A, Sawtell N M, Mahller Y Y, Stroup G, Collins M H, et al. Efficacy and safety of the oncolytic herpes simplex virus rRp450 alone and combined with cyclophosphamide. Molecular therapy: the journal of the American Society of Gene Therapy. 2008; 16:879-85.
22. Hong C S, Fellows W, Niranjan A, Alber S, Watkins S, Cohen J B, et al. Ectopic matrix metalloproteinase-9 expression in human brain tumor cells enhances oncolytic HSV vector infection. Gene therapy. 2010; 17:1200-5.
23. Zhang Y, Chao T, Li R, Liu W, Chen Y, Yan X, et al. MicroRNA-128 inhibits glioma cells proliferation by targeting transcription factor E2F3a. J Mol Med. 2009; 87:43-51.
24. Shi L, Cheng Z, Zhang J, Li R, Zhao P, Fu Z, et al. hsa-mir-181a and hsa-mir-181b function as tumor suppressors in human glioma cells. Brain Res. 2008; 1236: 185-93.
25. Silber J, Lim D A, Petritsch C, Persson A I, Maunakea A K, Yu M, et al. miR-124 and miR-137 inhibit proliferation of glioblastoma multiforme cells and induce differentiation of brain tumor stem cells. BMC Med. 2008; 6:14.
26. Maiorano N A, Mallamaci A. The pro-differentiating role of miR-124: indicating the road to become a neuron. RNA Biol. 7:528-33.
27. Lavon I, Zrihan D, Granit A, Einstein O, Fainstein N, Cohen M A, et al. Gliomas display a microRNA expression profile reminiscent of neural precursor cells. Neuro Oncol.12:422-33.
28. Karpowicz P, Willaime-Morawek S, Balenci L, DeVeale B, Inoue T, van der Kooy D. E-Cadherin regulates neural stem cell self-renewal. J Neurosci. 2009; 29:3885-96.
29. Katoh Y, Katoh M. Hedgehog signaling, epithelial-to-mesenchymal transition and miRNA (review). Int J Mol Med. 2008; 22:271-5.
30. Ocana O H, Nieto M A. A new regulatory loop in cancer-cell invasion. EMBO Rep. 2008; 9:521-2.
31. Verhaak R G, Hoadley K A, Purdom E, Wang V, Qi Y, Wilkerson M D, et al. Integrated genomic analysis identifies clinically relevant subtypes of glioblastoma characterized by abnormalities in PDGFRA, IDH1, EGFR, and NF1. Cancer cell.17:98-110.
32. Nduom E K, Hadjipanayis C G, Van Meir E G. Glioblastoma cancer stem-like cells: implications for pathogenesis and treatment. Cancer journal. 2012; 18:100-6.
33. He J, Liu Y, Lubman D M. Targeting glioblastoma stem cells: cell surface markers. Current medicinal chemistry. 2012; 19:6050-5.
34. Kambara H, Okano H, Chiocca E A, Saeki Y. An oncolytic HSV-1 mutant expressing ICP34.5 under control of a nestin promoter increases survival of animals even when symptomatic from a brain tumor. Cancer research. 2005; 65:2832-9.
35. Xia H, Cheung W K, Ng S S, Jiang X, Jiang S, Sze J, et al. Loss of brain-enriched miR-124 microRNA enhances stem-like traits and invasiveness of glioma cells. The Journal of biological chemistry. 2012; 287:9962-71.
36. Macdonald S J, Mostafa H H, Morrison L A, Davido D J. Genome sequence of herpes simplex virus 1 strain KOS. Journal of virology. 2012; 86:6371-2.
37. Kaji K, Norrby K, Paca A, Mileikovsky M, Mohseni P, Woltj en K. Virus-free induction of pluripotency and subsequent excision of reprogramming factors. Nature. 2009; 458:771-5.
38. Krisky D M, Marconi P C, Oligino T, Rouse R J, Fink D J, Glorioso J C. Rapid method for construction of recombinant HSV gene transfer vectors. Gene therapy. 1997; 4:1120-5.

Example 2

This Example describes arming a tumor targeted oHSV type 1 with matrix metalloproteinase 9 for enhanced vector distribution and killing activity.

Materials and Methods

Cell lines. Human glioblastoma SNB19, U251, U87 (kindly provided by Dr. H Okada, University of Pittsburgh), J/A, J/C, J/EGFR [9], African green monkey kidney Vero cells and 7b [15] cells were cultured by standard methods.

Cells were cultured in Dulbecco's modified Eagle's medium (Life technologies, Grand Island, NY) supplemented with 10% fetal bovine serum (Sigma. St. Louis, MO). Primary glioblastoma cell lines GBM169, OG2 (kindly provided by Dr. Balveen Kaur, Ohio State University), GBM30 were cultured as spheroids in Neurobasal medium supplemented with Glutamax, B27, human β-FGF, EGF, heparin and penicillin-streptomycin.

Plasmids. KGw BAC was generated from KGE-4: T124BAC by insertion of a Gateway cassette amplified from pcDNA3.1GW with primer (SEQ ID NO: 12)
5'-TGCCCGTCGCGCGTGTTTGATGTTAATAAATAACACATAAATTTGGC TGGCCACTAGTCCAGTGTGGTGG-3'
and (SEQ ID NO: 13)
5'-CTGAAATGCCCCCCCCCCCTTGCGGGCGGTCCATTAAAGACAACAA

ACAAATCCCCAGCATGCCTGCTATTGT-3'.

pEnCM was made by cloning the CAG promoter from plasmid pCAGH [10] into pEntr-MMP9. pEntr-MMP9 was made by cloning mmp9 cDNA from a previously reported plasmid, pCMV6-XL4-MMP9, into pEntrlA plasmid [13].

HSV genome engineering. KOS-37 BAC [14], containing the complete strain KOS HSV-1 genome on a bacterial artificial genome (BAC), was kindly provided by David Leib (Dartmouth Medical School, NH). The double Red recombination in E. coli [24] was used to introduce a series of modifications into KOS-37 BAC, a full-length genomic clone of the KOS strain of HSV-1 on a bacterial artificial chromosome (BAC) [14]. The product, KGBAC (FIG. 5A-5D), is deleted for the internal repeat (joint) region containing one copy each of the diploid genes ICP0, ICP34.5, LAT and ICP4 along with the promoter for the ICP47 gene.

KGwG4:T124BAC (referred to as KGw) was created from KGE-4:T124BAC (discussed in Example 1) by insertion of the Gateway cassette (from pcDNA3.1GW) and the bovine growth hormone polyadenylation sequence into the UL3-UL4 intergenic region through the Red/ET recombination technology (Gene Bridges GmbH, Heidelberg). The MMP9 expressing vector KMMP9G4:T124BAC (referred to as KMMP9) was derived from KGwG4:T124BAC by replacement of the GW cassette with the CAG promoter-MMP9 cassette from pEnCM by LR Clonase reaction. In order to produce the viruses, Vero 7b cells were transfected with either KGwG4:T124BAC or KMMP9G4:T124BAC. All recombinant vectors were confirmed by FIGE-mapping, PCR and DNA sequencing through relevant modified regions.

Virus growth and purification. BAC DNAs were converted to infectious virus by transfection of Vero 7b cells using Lipofectamine™ LTX Reagent (Invitrogen). Biological titers of virus stocks (PFU/mL) were established on Vero cells; physical titers in genome copies (gc)/mL were determined by quantitative real-time PCR (qPCR) for the viral gD gene, as described below.

qPCR for viral genomes. DNA was extracted from virus stocks using the DNeasy Blood & Tissue kit (Qiagen, Valencia, CA) according to the manufacturer's procedure. A standard curve for qPCR was generated on DNA from a pENTR1A (Invitrogen) plasmid containing the complete HSV-1 (strain KOS) gD coding sequence (pE-gD18) using the protocol described in the Applied Biosystems StepOne™ and StepOnePlus™ Real-Time PCR Systems manual. Primers and probe sequences are listed: gD forward:

```
                                          (SEQ ID NO: 14)
    5'-CCCCGCTGGAACTACTATGACA-3';

gD reverse:
                                          (SEQ ID NO: 15)
    5'-GCATCAGGAACCCCAGGTT-3';

probe:
                                          (SEQ ID NO: 16)
    5'-FAM-TTCAGCGCCGTCAGCGAGGA-TAMRA-3'
```

Western blotting. Cells were lysed in 1% NP40 buffer, lysates electrophoresed through 10% SDS-polyacrylamide gels, and protein blots reacted with polyclonal anti-MMP-9 antibody (1:1000 dilution) (Abcam, Cambridge, MA) or with anti-gD antibody (1:2000) (Santa Cruz, CA) and HRP-conjugated anti-rabbit secondary antibody (Sigma, St. Louis, MO). Blots were developed with chemiluminescence substrate (Amersham Pharmacia, Piscataway, NJ). The lower portion of each blot was reacted with polyclonal anti-beta-tubulin antibody (1:3000) (Sigma, St. Louis, MO) to detect loading differences. Blots were developed with SuperSignal West Dura Chemiluminescent Substrate (Thermo Scientific, Rockford, IL).

Gelatin zymography. Samples were not treated with reducing agent nor heated before separated on a 10% SDS-polyacrylamide gel containing 0.2% gelatin. The gel was washed in zymography washing buffer (10 mM Tris pH 7.5, 2.5% Triton X-100), incubated at 37° C. for 16 h in incubation buffer (50 mM Tris pH 7.5, 5 mM CaCl2, 1 µM ZnCl2), stained with 1% Coomassie brilliant blue R-250 and destained with destaining buffer (4% methanol, 8% acetic acid) [13].

Entry assay. J/A, J/C and J/EGFR cells were infected at 10,000, 1,000 or 100 gc/cell with KMMP9, KGw or KG (expressing gD:wt) for 6 hours and immunostained with monoclonal mouse anti-ICP4 (1:300; Santa Cruz Biotechnology) and Cy3-conjugated sheep anti-mouse IgG (1:400; Sigma) [9].

MTT assay. Cells were seeded in 48 well plates and infected at 100 gc/cell (MOI 0.2) for 3 or 6 days. Cells were then treated with 0.5 mg/ml of MTT (Sigma) solution at 37° C. for 3 hours. After removal of MTT solution, 100% DMSO was added and OD570 was recorded by a Wallac microplate reader (Perkin Elmer, Waltham, MA). Percent cell survival was calculated as 100%×OD (infected)/OD (uninfected)

Spheroid culture and confocal imaging. Spheroids were dissociated and counted. 3,000 cells were grown individually in suspension for 2 days until spheroids formed. Each spheroid was infected with 1000 pfu or $4 \times 10^7$ gc of KMMP9 or KGw separately in micro assay plates. eGFP images were acquired daily with a fluorescence microscope. For confocal imaging, spheroids were transferred to glass bottom dishes (Willco wells, Amsterdam, the Netherlands) upon infection. At 5 dpi, spheroids were fixed in 4% paraformaldehyde, treated with mounting medium with DAPI (Vector Laboratories, Burlingame, CA) and Z section images were obtained with FV1000 confocal imaging system (Olympus, Miami, FL).

Tumor model and treatment. 3-4 week-old BALB/c athymic nu/nu mice were purchased from Charles River Laboratory (Wilmington, MA) and housed in a BSL2 facility. All animal procedures were performed in accordance with the requirements and recommendations in the Guide for the Care and the Use of Laboratory Animals (Institute for Laboratory Animal Research, 1985) as approved by the University of Pittsburgh Institutional Animal Care and Use Committee (IACUC).

Intracranial implantation of $2 \times 10^5$ human GBM30 cells into nude mice was performed as described [9]. At 5 or 10 dpi, $5.65 \times 10^9$ genome copies of KMMP9, KGw, or PBS (n=3-4/group) were inoculated at the same coordinates to which tumor cells were injected (0.5 mm anterior 2 mm lateral (right) 3 mm deep to bregma), as also described [9]. Animal health and well-being were monitored and animals were euthanized when showing signs of morbidity.

MRI imaging. Several mice were randomly selected from each treatment group (KMMP9, KGw, PBS). Animals were imaged 1 day before treatment (9 days after GBM30 implantation) and on days 3, 6, 9 and 13 post-treatment. Imaging was performed using a Bruker BioSpec 94/30 magnet (Bruker BioSpin, Karlsruhe, Germany), a 2.0 cm diameter receive-only mouse brain coil and a 70 mm diameter linear volume coil. Anesthetized mice were injected with 0.1 mmol/kg Magnevist (Bayer Health Care Pharmaceuticals, Wayne, NJ) intraperitoneally and T2-weighted images (repetition time=3,500 ms, echo time=12 ms, rare factor=8, navgs=4) were acquired coronally across the region of interest on a 400 MHz Bruker horizontal bore magnet running Paravision 4.0 (Bruker Biospin, Billerica, MA).

Statistical analysis. Unpaired t test with Welch's correction was performed using GraphPad Prism version 6.01 for Windows (GraphPad Software, La Jolla, CA; www.graphpad.com). Animal survival data were charted as Kaplan-Meier plots and compared by Mantel-Cox log-rank test using the same software.

Results

Construct and Characterization of Retargeted-miR Controlled Vectors Expressing MMP9

Figure 5A:
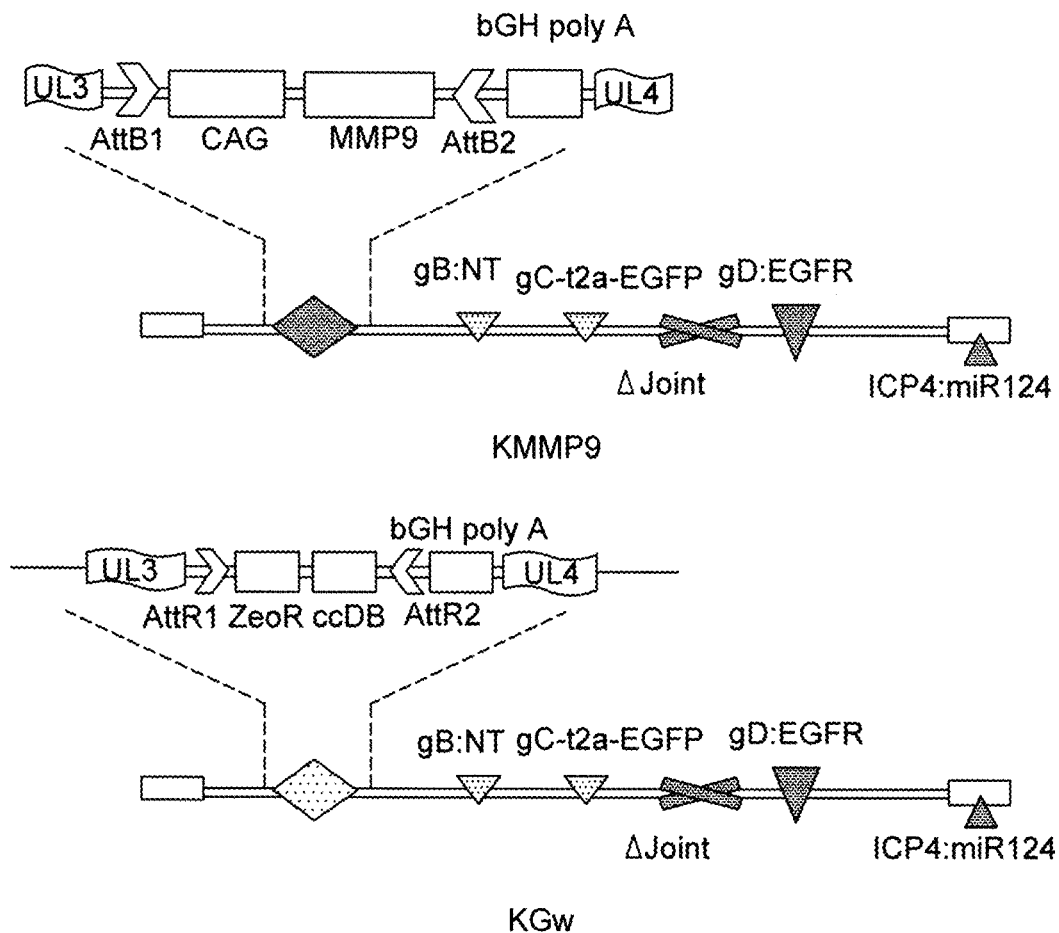

Vector engineering and design for this study are diagrammed in FIG. 5A and include multiple modifications that are intended to avoid altering any viral lytic functions and thus maximize the replication and lytic activity in tumor cells while avoiding virus growth in normal brain.

A Gateway cassette (Gw) and bovine growth hormone polyadenylation sequence were inserted between UL3 and UL4 loci of KGE-4:T124 (described in Example 1) to create KGwG4:T124BAC (referred to here as KGw, control vector); the oncolytic vector expressing MMP9 was obtained by replacing the Gateway cassette with the MMP9 gene driven by the CAG (CMV chicken β actin) promoter (KMMP9G4: T124BAC referred to here as KMMP9).

Figure 5B:
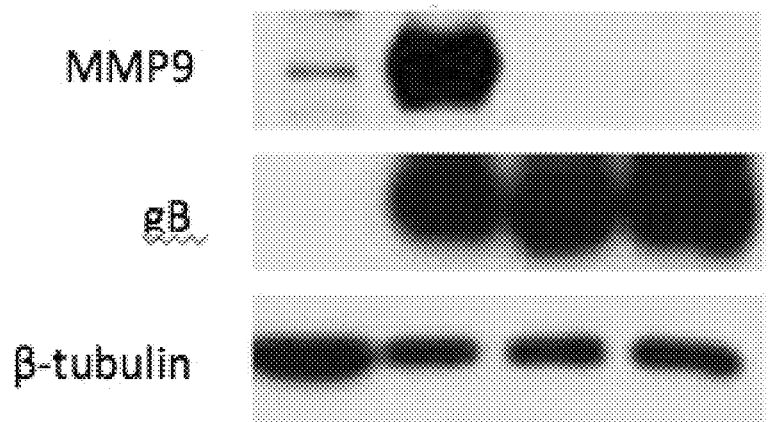
Figure 5C:
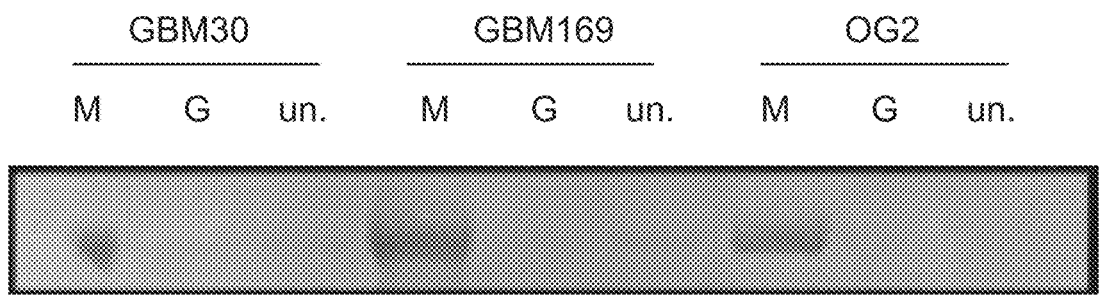
Figure 5D:
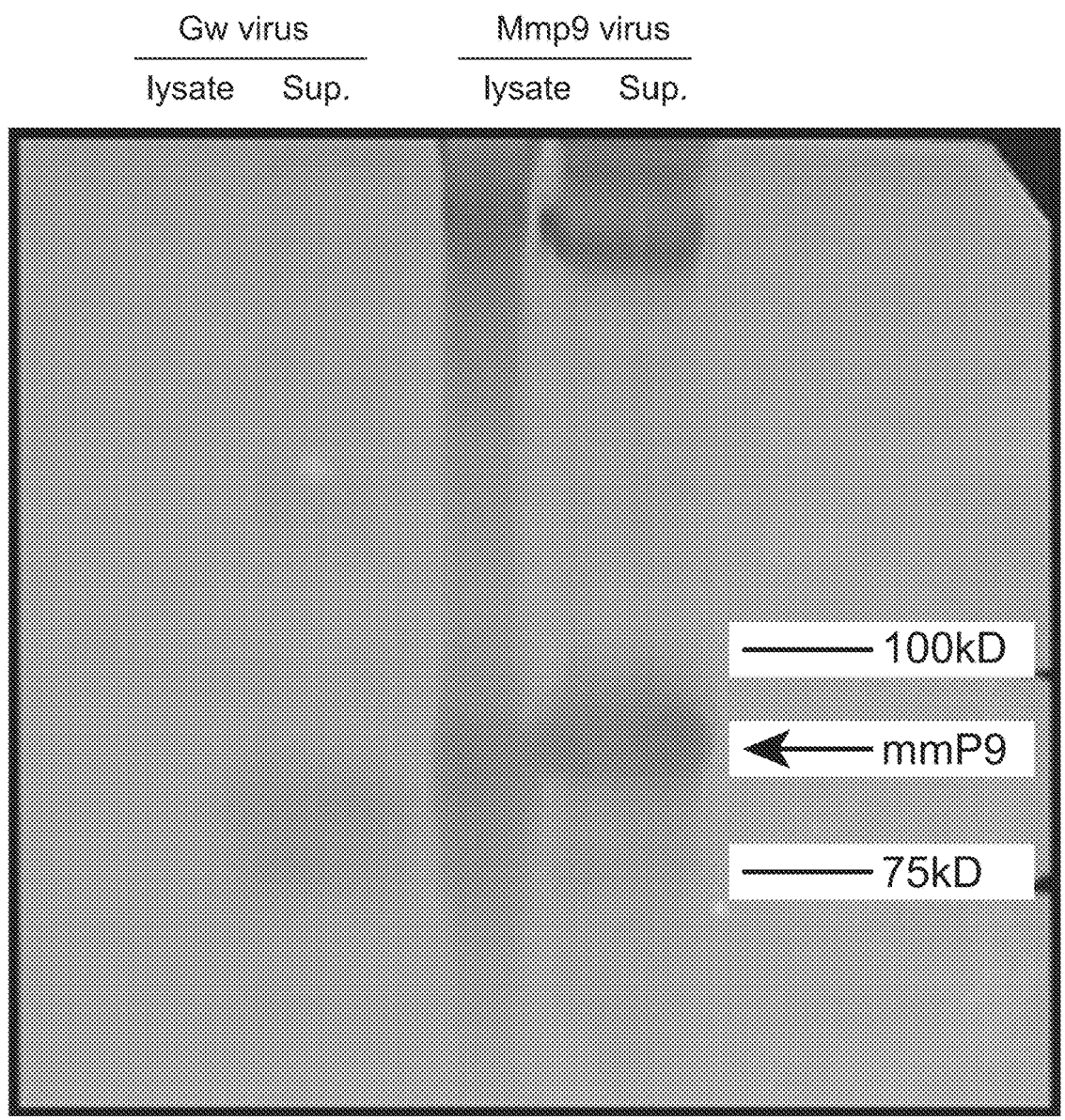

Western blot analysis of Vero cells infected with KMMP9 confirmed the correct expression of MMP9 (FIG. 5B). Gelatin zymography showed greater gelatinase activity in three primary GBM lines, GBM 30, GBM169 and OG2, infected with KMMP9 compared to the cells infected with the control vector (FIG. 5C) and in the supernatant of KMMP9-infected Vero cells compared to control-infected Vero cells (FIG. 5D).

We then determined whether MMP9 expression affected virus entry through recognition of the Epidermal Growth Factor Receptor (EGFR). The cell lines tested for virus entry included EGFR-transduced J1.1-2 cells (J/EGFR) (Nakano et al., Virol., 413: 12-18 (2011)) that are resistant to wt HSV due to the absence of gD receptors, J/A cells expressing human HVEM (Uchida et al., *J. Virol.* 83: 2951-2961 (2009)), and J/C cells expressing human nectin-1 (Frampton et al., *J. Virol.*, 81: 10879-889 (2007)); HVEM and nectin-1 are natural receptors for wt gD. Virus entry was detected by immunostaining for the immediate early HSV protein ICP4 6 hours post infection. As shown in FIG. 6A, entry of the EGFR-retargeted viruses KMMP9 and KGw into J/EGFR cells was as efficient as entry of the parental HSV-1 vector expressing gD:wt into J/A or J/C cells. Neither of the retargeted viruses detectably entered J/A or J/C cells even at high virus input (10,000 gc/cell), demonstrating that the MMP9 expression does not affect the efficiency or specificity of retargeted vector infection.

We also assessed if MMP9 expression could affect virus replication in human GBM cells in culture. The results (FIGS. 6B and 6C) showed that KMMP9 replicated with similar kinetics as KGw in spheroids of two primary glioblastoma lines, GBM169 and GBM30, and the yields of the 2 viruses (measured by qPCR) were not substantially different at any time point.

To evaluate the oncolytic activity of KMMP9, HSV-permissive human glioma lines known to express EGFR, including U87MG, SNB19, and GBM30, were infected with an MOI of 0.005 (100 gc/cell) and cell viability was determined by 3-(4,5-dimethylthiazol-2-yl)-2,5-diphenyltertrazolium bromide (MTT) assay at 3 (FIG. 7A) and 7 days post infection (FIG. 7B). At the latter time point, KMMP9 showed significantly higher killing of 2 the cell lines compared to that of KGw, suggesting that MMP9 could augment vector-mediated oncolysis.

MMP-9 Increases HSV Infectivity in Spheroid Culture.

Figure 8A:
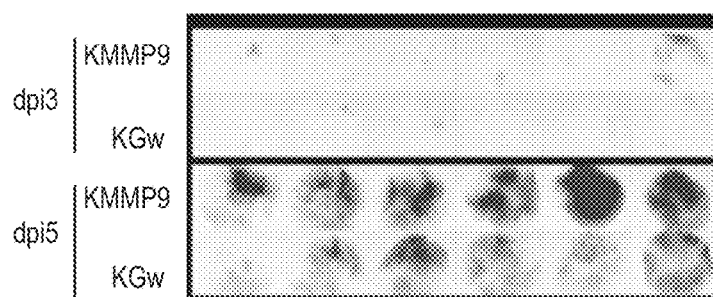
Figure 8B:
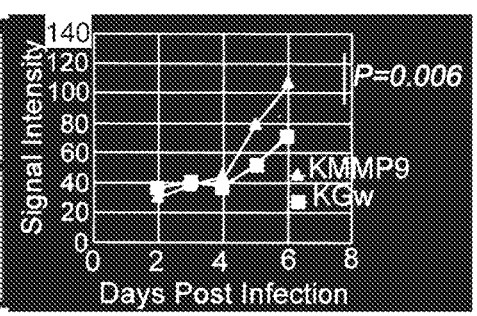

To assess the effect of increased cellular expression of MMP-9 on HSV spread in tumor-cell spheroids, GBM30 and GBM169 cells were cultured as a single spheroids and infected with KMMP9 or KGw virus (FIG. 8A). At 5 dpi, KMMP9 showed enhanced distribution of vector-expressed eGFP compared to KGw. Quantification of eGFP positive cells in each spheroid demonstrated an increase of approximately 1.5 fold at 6 dpi in KM1V1P9-over KGw-infected spheroids (FIG. 8B; P=0.006).

Figure 8C:
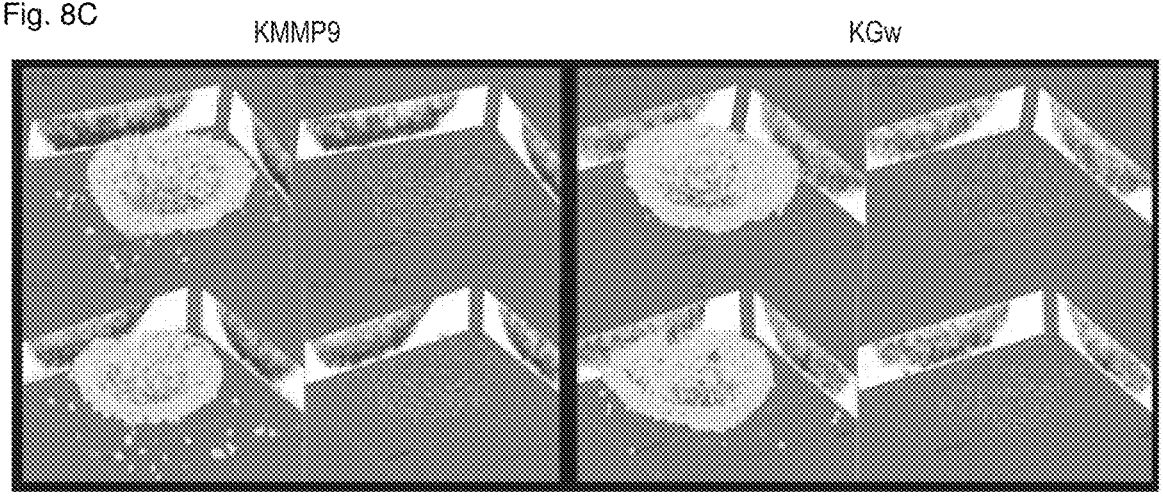
Figure 8D:
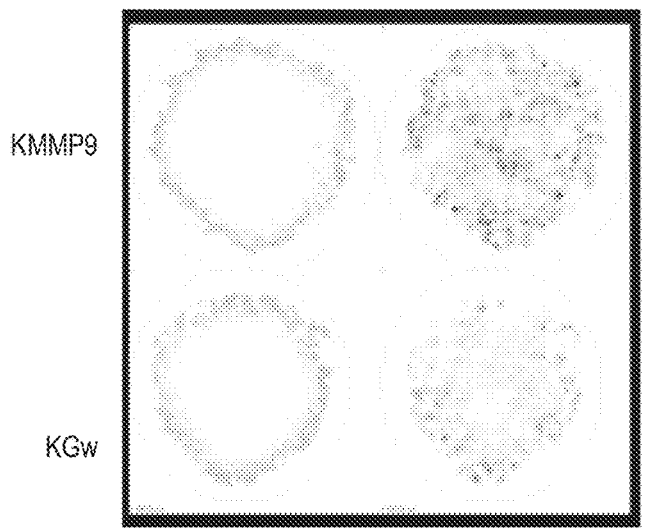
Figure 8E:
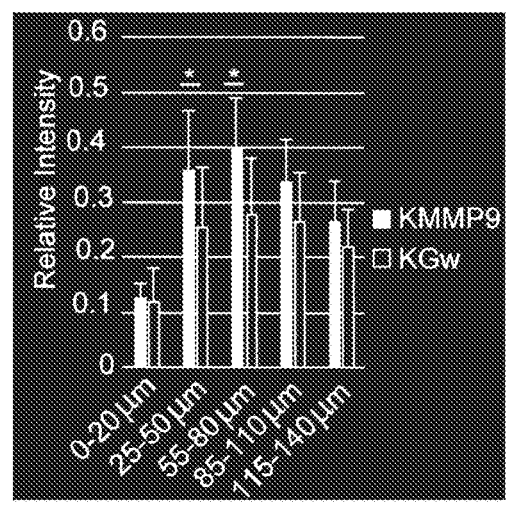

In order to further quantify the effect of MMP9 on HSV infectivity of primary tumor-derived spheroids, GBM30 cells were infected with either KMMP9 or KGw, and the eGFP expressed by the vector was imaged by confocal microscopy as a means to assess virus penetration and infectivity. 3D reconstruction from 5 μm Z section stacks revealed enhanced relative infectivity of KMMP9 compared with KGw inside the spheroids. (FIG. 8C). We also examined infectivity differences in 5 segments of each spheroid in terms of depth on the Z axis (FIGS. 8D and 8E) (from bottom up 0-20 μm, 25-50 μm, 55-80 μm, 85-100 μm, 105-120 μm and 125-140 μm). While no difference was found in the outermost segment (0-20 μm) (FIGS. 8D and 8E), KMMP9 showed significantly higher infectivity than KGw deeper into the spheroids (25-50 and 50-85 μm, P<0.05), suggesting that MMP9 enhanced vector spreading throughout the spheroids. A significant difference was also found when all segments were compared between spheroids (paired t-test, P=0.013).

The MMP9 Oncolytic Vector is Highly Effective in GBM Therapy in Mice.

We previously showed that GBM30 consistently established a lethal tumor in nude mice leading to animal death within 20 days post-tumor cell inoculation [9]. We used patient-derived, sphere-forming GBM30 cells to establish aggressive intracranial tumors in nude mice [9]. Animals were observed daily and euthanized when showing signs of morbidity. Similar to our published results, mice injected with PBS 5 d after tumor-cell inoculation at the same stereotactic coordinates died within weeks of tumor-cell implantation (median 18 d; FIG. 9). In contrast, tumor treatments using either the MMP9 expressing virus, KMMP9, or the control virus KGw, protected half of the animals for at least 35 days and the median survival times for these two groups were comparable (29 and 31.5 d, respectively; P=0.61, log-rank test). These results showed that 50% of the MMP9 treated animals survived up to 35 days compared to 18 days without treatment (FIG. 9).

In a parallel independent experiment, the antitumor efficacy of KMMP9 and KGw were compared with mock (PBS) treatment in the orthotopic GBM30 xenograft model by injecting the vectors 10 days after tumor inoculation. Mice were imaged by magnetic resonance imaging (MRI) for changes in tumor size 1 day before treatment and again on days 3, 6, 9 and 13 post treatment. FIG. 10A shows the T2-weighted images of an example from each group. Comparison of single animals from each group that had comparable tumor volumes at the time of treatment initiation, it is clear that MMP9 had a stronger oncolytic effect than the KGw vector (FIG. 10B).

References for Example 2

1. Grossman, S. A., et al., *Survival of patients with newly diagnosed glioblastoma treated with radiation and temozolomide in research studies in the United States.* Clin Cancer Res, 2010. 16(8): p. 2443-9.
2. Assi, H., et al., *Gene therapy for brain tumors: basic developments and clinical implementation.* Neurosci Lett, 2012. 527(2): p. 71-7.
3. Friedman, G. K., et al., *Herpes simplex virus oncolytic therapy for pediatric malignancies.* Mol Ther, 2009. 17(7): p. 1125-35.
4. Mohyeldin, A. and E. A. Chiocca, *Gene and viral therapy for glioblastoma: a review of clinical trials and future directions.* Cancer J, 2012. 18(1): p. 82-8.
5. Campadelli-Fiume, G., et al., *Rethinking herpes simplex virus: the way to oncolytic agents.* Rev Med Virol, 2011. 21(4): p. 213-26.
6. Broberg, E. K. and V. Hukkanen, *Immune response to herpes simplex virus and gamma134.5 deleted HSV vectors.* Curr Gene Ther, 2005. 5(5): p. 523-30.
7. Aghi, M., et al., *Oncolytic herpes virus with defective ICP6 specifically replicates in quiescent cells with homozygous genetic mutations in p16.* Oncogene, 2008. 27(30): p. 4249-54.
8. Navaratnarajah, C. K., et al., *Targeted entry of enveloped viruses: measles and herpes simplex virus I.* Curr Opin Virol, 2012. 2(1): p. 43-9.
9. Uchida, H., et al., *Effective treatment of an orthotopic xenograft model of human glioblastoma using an EGFR-retargeted oncolytic herpes simplex virus.* Mol Ther, 2013. 21(3): p. 561-9.
10. Uchida, H., et al., *A double mutation in glycoprotein gB compensates for ineffective gD-dependent initiation of herpes simplex virus type 1 infection.* J Virol, 2010. 84(23): p. 12200-9.
11. Payne, L. S. and P. H. Huang, *The pathobiology of collagens in glioma.* Mol Cancer Res, 2013. 11(10): p. 1129-40.
12. Mok, W., Y. Boucher, and R. K. Jain, *Matrix metalloproteinases-1 and -8 improve the distribution and efficacy of an oncolytic virus.* Cancer Res, 2007. 67(22): p. 10664-8.

13. Hong, C. S., et al., *Ectopic matrix metalloproteinase-9 expression in human brain tumor cells enhances oncolytic HSV vector infection.* Gene Ther, 2010. 17(10): p. 1200-5.
14. Gierasch, W. W., et al., *Construction and characterization of bacterial artificial chromosomes containing HSV-1 strains 17 and KOS.* J Virol Methods, 2006. 135(2): p. 197-206.
15. Krisky, D. M., et al., *Deletion of multiple immediate-early genes from herpes simplex virus reduces cytotoxicity and permits long-term gene expression in neurons.* Gene Ther, 1998. 5(12): p. 1593-603.
16. Szymczak, A. L. and D. A. Vignali, *Development of 2A peptide-based strategies in the design of multicistronic vectors.* Expert Opin Biol Ther, 2005. 5(5): p. 627-38.
17. Miao, H., et al., *EphA2 promotes infiltrative invasion of glioma stem cells in vivo through cross-talk with Akt and regulates stem cell properties.* Oncogene, 2014.
18. Yin, A. A., et al., *The treatment of glioblastomas: a systematic update on clinical Phase III trials.* Crit Rev Oncol Hematol, 2013. 87(3): p. 265-82.
19. Wong, J., et al., *Targeted oncolytic herpes simplex viruses for aggressive cancers.* Curr Pharm Biotechnol, 2012. 13(9): p. 1786-94.
20. Wakimoto, H., et al., *Effects of innate immunity on herpes simplex virus and its ability to kill tumor cells.* Gene Ther, 2003. 10(11): p. 983-90.
21. McKee, T. D., et al., *Degradation of fibrillar collagen in a human melanoma xenograft improves the efficacy of an oncolytic herpes simplex virus vector.* Cancer Res, 2006. 66(5): p. 2509-13.
22. Yun, C. O., *Overcoming the extracellular matrix barrier to improve intratumoral spread and therapeutic potential of oncolytic virotherapy.* Curr Opin Mol Ther, 2008. 10(4): p. 356-61
23. Dmitrieva, N., et al., *Chondroitinase ABC I-mediated enhancement of oncolytic virus spread and antitumor efficacy.* Clin Cancer Res, 2011. 17(6): p. 1362-72.
24. Tischer, B. K., et al., *Two-step red-mediated recombination for versatile high-efficiency markerless DNA manipulation in Escherichia coli.* Biotechniques, 2006. 40(2): p. 191-7.
25. Ishida, D., et al., *Enhanced cytotoxicity with a novel system combining the paclitaxel-2'-ethylcarbonate prodrug and an HSV amplicon with an attenuated replication-competent virus, HE 10 as a helper virus.* Cancer Lett, 2010. 288(1): p. 17-27.

All references, including publications, patent applications, and patents, cited herein are hereby incorporated by reference to the same extent as if each reference were individually and specifically indicated to be incorporated by reference and were set forth in its entirety herein. The contents of U.S. patent application Ser. No. 13/641,649 (National Phase of PCT/US2011/032923), which has been published as US 2013/0096186 and WO 2011/130749 and which claims priority to U.S. Provisional Patent Application 61/325,137 also are incorporated herein in their entirety, and attention is particularly drawn to paragraphs [0039], [0040], and [0041] of US 2013/0096186. Also incorporated by reference in its entirety is Mazzacurati et al, Mol. Ther. 2014 Sep. 9. doi: 10.1038/mt.2014.177. [Epub ahead of print]

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A recombinant herpes simplex virus (HSV), comprising:
   (a) a mutation of glycoprotein B (gB) at position 285 or 549; and
   (b) a plurality of copies of one or more microRNA target sequences inserted into a locus of one or more HSV genes required for HSV replication,
   wherein expression of one or more genes in the internal repeat (joint) region in the HSV genome is silenced, and
   wherein the internal repeat (joint) region comprises one copy of the ICP0, ICP34.5, LAT, and ICP4 genes and the promoter of the ICP47 gene.

2. The HSV of claim 1, wherein the one or more genes in the internal repeat (joint) region that have silenced expression comprises the ICP0 gene or the ICP34.5 gene.

3. The HSV of claim 1, wherein the expression is silenced by deletion or limited mutagenesis of the one or more genes in the internal repeat (joint) region.

4. The HSV of claim 1, wherein the one or more microRNA target sequences are inserted in the 3' untranslated region (3' UTR) of the one or more HSV genes.

5. The HSV of claim 1, comprising two or more copies of the microRNA target sequences inserted into the locus of the one or more HSV genes.

6. The HSV of claim 5, comprising 4 copies of the microRNA target sequences inserted into the locus of the one or more HSV genes.

7. The HSV of claim 1, wherein at least one of the one or more microRNA target sequences is a target sequence for miR-124.

8. The HSV of claim 7, wherein the target sequence for miR-124 is present in an ICP4 gene.

9. The HSV of claim 1, comprising a plurality of copies of at least two microRNA target sequences selected from the group consisting of a miR-122 target sequence, a miR-124 target sequence, a miR-128 target sequence, a miR-137 target sequence, and a miR-199 target sequence.

10. The HSV of claim 1, wherein the mutation of the gB at position 285 or 549 is a missense mutation selected from the group consisting of D285N and A549T.

11. The HSV of claim 1, wherein the HSV comprises a mutation of the gB at both positions 285 and 549.

12. The HSV of claim 1, further comprising a non-HSV ligand displayed on the surface of the HSV envelope, which is specific for a molecule present on the surface of a cancer cell.

13. The HSV of claim 1, further comprising a transgene that encodes an oncolytic factor, a protein or polypeptide that induces patient immune response against cancer, or a protein or polypeptide that enhances the lateral spread of the HSV.

14. A nucleic acid encoding the HSV of claim 1.

15. A viral stock comprising the HSV of claim 1, wherein the viral stock has a viral titer of at least $10^5$ plaque-forming units (pfu).

16. A composition comprising:

(a) the HSV of claim 1, a nucleic acid encoding the HSV, or a viral stock comprising the HSV; and (b) a pharmaceutically acceptable carrier.

17. A method of killing a cancerous cell, comprising exposing the cancerous cell to the HSV of claim 1, a nucleic acid encoding the HSV, or a viral stock comprising the HSV under conditions sufficient for the HSV, the nucleic acid, or the viral stock to infect the cancerous cell, whereby replication of the HSV within the cancerous cell results in death of the cancerous cell.

18. The method of claim 17, wherein the cell is in vivo.

19. The method of claim 17, wherein the cell is a human cell.

20. The method of claim 17, wherein the cell is within a tumor.

21. The method of claim 20, wherein the tumor is glioblastoma multiforme.

22. The method of claim 17, wherein the cell is within the brain of an animal.

23. The method of claim 22, wherein the HSV, the nucleic acid, or the viral stock is exposed to the cell by intracranially injecting the HSV, the nucleic acid, or the viral stock to the animal.

24. A recombinant Herpes Simplex Virus (HSV), comprising:
  (a) a non-HSV ligand displayed on the surface of the HSV envelope, which is specific for a molecule present on the surface of a cancer cell; and
  (b) a plurality of copies of one or more microRNA target sequences inserted into a locus of one or more HSV genes required for HSV replication,
  wherein the expression of one or more genes in the internal repeat (joint) region in the HSV genome is silenced, and wherein the internal repeat (joint) region comprises one copy of the ICP0, ICP34.5, LAT, and ICP4 genes and the promoter of the ICP47 gene.

25. The HSV of claim 24, wherein the one or more genes in the internal repeat (joint) region that have silenced expression comprises the ICP0 gene or the ICP34.5 gene.

26. The HSV of claim 24, wherein the expression is silenced by deletion or limited mutagenesis of the one or more genes in the internal repeat (joint) region.

27. The HSV of claim 24, wherein the ligand is incorporated into a viral envelope glycoprotein exposed on the HSV surface.

28. The HSV of claim 27, wherein the viral envelope glycoprotein is gD or gC.

29. The HSV of claim 28, wherein the ligand is incorporated between residues 1 and 25 of gD.

30. The HSV of claim 24, wherein the non-HSV ligand is capable of specifically binding EGFR or EGFRvIII.

31. The HSV of claim 24, wherein the ligand is a single-chain antibody (scFv), a peptide, a non-peptide hormone, or a growth factor that binds a cellular receptor.

32. The HSV of claim 24, comprising two or more copies of the microRNA target sequences inserted into the locus of the one or more HSV genes.

33. The HSV of claim 32, comprising 4 copies of the microRNA target sequences inserted into the locus of the one or more HSV genes.

34. The HSV of claim 32, wherein the two or more copies of the microRNA target sequences are separated by spacers of four or more nucleotides within the HSV genome.

35. The HSV of claim 24, wherein the one or more microRNA target sequences are inserted in the 3' untranslated region (3' UTR) of the one or more HSV genes.

36. The HSV of claim 24, wherein at least one of the one or more microRNA target sequences is a target sequence for miR-124.

37. The HSV of claim 24, comprising a plurality of copies of at least two microRNA target sequences selected from the group consisting of a miR-122 target sequence, a miR-124 target sequence, a miR-128 target sequence, a miR-137 target sequence, and a miR-199 target sequence.

38. The HSV of claim 24, further comprising a mutant HSV gB or gH glycoprotein that facilitates vector entry through non-canonical receptors.

39. The HSV of claim 24, further comprising a transgene that encodes an oncolytic factor, a protein or polypeptide that induces patient immune response against cancer, or a protein or polypeptide that enhances the lateral spread of the HSV.

40. A nucleic acid encoding the HSV of claim 24.

41. A viral stock comprising the HSV of claim 24, wherein the viral stock has a viral titer of at least $10^5$ plaque-forming units (pfu).

42. A composition comprising:
  (a) the HSV of claim 24, a nucleic acid encoding the HSV, or a viral stock comprising the HSV; and
  (b) a pharmaceutically acceptable carrier.

43. A method of killing a cancerous cell, comprising exposing the cancerous cell to the HSV of claim 24, a nucleic acid encoding the HSV, or a viral stock comprising the HSV under conditions sufficient for the HSV, the nucleic acid, or the viral stock to infect the cancerous cell, whereby replication of the HSV within the cancerous cell results in death of the cancerous cell.

44. The method of claim 43, wherein the cell is in vivo.

45. The method of claim 43, wherein the cell is a human cell.

46. The method of claim 43, wherein the cell is within a tumor.

47. The method of claim 46, wherein the tumor is glioblastoma multiforme.

48. The method of claim 43, wherein the cell is within the brain of an animal.

49. The method of claim 48, wherein the HSV, the nucleic acid, or the viral stock is exposed to the cell by intracranially injecting the HSV, the nucleic acid, or the viral stock to the animal.

\* \* \* \* \*

SEQUENCE LISTING

```
<160> NUMBER OF SEQ ID NOS: 16

<210> SEQ ID NO 1
<211> LENGTH: 115
<212> TYPE: DNA
<213> ORGANISM: Artificial Sequence
<220> FEATURE:
<223> OTHER INFORMATION: primer

<400> SEQUENCE: 1
ctagtggcat tcaccgcgtg ccttatagta ccagggcatt caccgcgtgc cttaaggatc      60
ctggcattca ccgcgtgcct taatgactgc ggcattcacc gcgtgcctta gagct         115
```

```
<210> SEQ ID NO 2
<211> LENGTH: 154
<212> TYPE: DNA
<213> ORGANISM: Artificial Sequence
<220> FEATURE:
<223> OTHER INFORMATION: primer

<400> SEQUENCE: 2
ctagtgcggc cgcgtctcgg gaccgcactc gttatcgaat agtctgacta caacttagta      60
ccagatcgaa tagtctgact acaactagga tcctatcgaa tagtctgact acaactatga     120
ctgcatcgaa tagtctgact acaactctcg agct                                 154

<210> SEQ ID NO 3
<211> LENGTH: 29
<212> TYPE: DNA
<213> ORGANISM: Artificial Sequence
<220> FEATURE:
<223> OTHER INFORMATION: primer

<400> SEQUENCE: 3
tcgaggatcc tgtcagtgcg cacgcacac                                        29

<210> SEQ ID NO 4
<211> LENGTH: 32
<212> TYPE: DNA
<213> ORGANISM: Artificial Sequence
<220> FEATURE:
<223> OTHER INFORMATION: primer

<400> SEQUENCE: 4
tcgaggatcc aaacacccga ggaaatgaaa ag                                    32

<210> SEQ ID NO 5
<211> LENGTH: 22
<212> TYPE: DNA
<213> ORGANISM: Artificial Sequence
<220> FEATURE:
<223> OTHER INFORMATION: primer

<400> SEQUENCE: 5
ccccgctgga actactatga ca                                               22

<210> SEQ ID NO 6
<211> LENGTH: 107
<212> TYPE: DNA
<213> ORGANISM: Artificial Sequence
<220> FEATURE:
<223> OTHER INFORMATION: primer

<400> SEQUENCE: 6
ctaaggcacg cggtgaatgc cgcagtcatt aaggcacgcg gtgaatgcca ggatccttaa      60
ggcacgcggt gaatgccctg gtactataag gcacgcggtg aatgcca                  107

<210> SEQ ID NO 7
<211> LENGTH: 146
<212> TYPE: DNA
<213> ORGANISM: Artificial Sequence
<220> FEATURE:
<223> OTHER INFORMATION: primer

<400> SEQUENCE: 7
cgagagttgt agtcagacta ttcgatgcag tcatagttgt agtcagacta ttcgatagga      60
tcctagttgt agtcagacta ttcgatctgg tactaagttg tagtcagact attcgataac     120
```

```
gagtgcggtc ccgagacgcg gccgca                                          146
```

<210> SEQ ID NO 8
<211> LENGTH: 27
<212> TYPE: DNA
<213> ORGANISM: Artificial Sequence
<220> FEATURE:
<223> OTHER INFORMATION: primer

<400> SEQUENCE: 8

```
tgcagctagc cagacccctc ccctcgc                                          27
```

<210> SEQ ID NO 9
<211> LENGTH: 32
<212> TYPE: DNA
<213> ORGANISM: Artificial Sequence
<220> FEATURE:
<223> OTHER INFORMATION: primer

<400> SEQUENCE: 9

```
tcgagctagc gctcagcgag cagcaagagt tc                                    32
```

<210> SEQ ID NO 10
<211> LENGTH: 19
<212> TYPE: DNA
<213> ORGANISM: Artificial Sequence
<220> FEATURE:
<223> OTHER INFORMATION: primer

<400> SEQUENCE: 10

```
gcatcaggaa ccccaggtt                                                   19
```

<210> SEQ ID NO 11
<211> LENGTH: 20
<212> TYPE: DNA
<213> ORGANISM: Artificial Sequence
<220> FEATURE:
<223> OTHER INFORMATION: probe

<400> SEQUENCE: 11

```
ttcagcgccg tcagcgagga                                                  20
```

<210> SEQ ID NO 12
<211> LENGTH: 70
<212> TYPE: DNA
<213> ORGANISM: Artificial Sequence
<220> FEATURE:
<223> OTHER INFORMATION: primer

<400> SEQUENCE: 12

```
tgcccgtcgc gcgtgtttga tgttaataaa taacacataa atttggctgg ccactagtcc      60
agtgtggtgg                                                             70
```

<210> SEQ ID NO 13
<211> LENGTH: 73
<212> TYPE: DNA
<213> ORGANISM: Artificial Sequence
<220> FEATURE:
<223> OTHER INFORMATION: primer

<400> SEQUENCE: 13

```
ctgaaatgcc ccccccccct tgcgggcggt ccattaaaga caacaaacaa atccccagca      60
tgcctgctat tgt                                                         73
```

```
<210> SEQ ID NO 14
<211> LENGTH: 22
<212> TYPE: DNA
<213> ORGANISM: Artificial Sequence
<220> FEATURE:
<223> OTHER INFORMATION: primer

<400> SEQUENCE: 14
ccccgctgga actactatga ca                                              22

<210> SEQ ID NO 15
<211> LENGTH: 19
<212> TYPE: DNA
<213> ORGANISM: Artificial Sequence
<220> FEATURE:
<223> OTHER INFORMATION: primer

<400> SEQUENCE: 15
gcatcaggaa ccccaggtt                                                  19

<210> SEQ ID NO 16
<211> LENGTH: 20
<212> TYPE: DNA
<213> ORGANISM: Artificial Sequence
<220> FEATURE:
<223> OTHER INFORMATION: probe

<400> SEQUENCE: 16
ttcagcgccg tcagcgagga                                                 20
```